United States Patent
Jay et al.

(10) Patent No.: US 9,029,328 B2
(45) Date of Patent: May 12, 2015

(54) METHODS FOR CARDIOPROTECTION AND CARDIOREGENERATION WITH DIMERS OF EGF FAMILY LIGANDS

(75) Inventors: Steven M. Jay, Cambridge, MA (US); Linda G. Griffith, Cambridge, MA (US); Richard T. Lee, Weston, MA (US)

(73) Assignees: The Brigham and Women's Hospital, Inc., Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/636,578

(22) PCT Filed: Mar. 24, 2011

(86) PCT No.: PCT/US2011/029799
§ 371 (c)(1),
(2), (4) Date: Apr. 2, 2013

(87) PCT Pub. No.: WO2011/119836
PCT Pub. Date: Sep. 29, 2011

(65) Prior Publication Data
US 2013/0196911 A1    Aug. 1, 2013

Related U.S. Application Data

(60) Provisional application No. 61/317,094, filed on Mar. 24, 2010.

(51) Int. Cl.
| | | |
|---|---|---|
| *A61P 9/04* | (2006.01) | |
| *A61K 38/22* | (2006.01) | |
| *A61K 38/16* | (2006.01) | |

(Continued)

(52) U.S. Cl.
CPC .......... *A61K 38/1808* (2013.01); *A61K 38/1709* (2013.01); *A61K 38/1883* (2013.01); *C07K 14/485* (2013.01); *C07K 2319/00* (2013.01)

(58) Field of Classification Search
None
See application file for complete search history.

(56) References Cited

U.S. PATENT DOCUMENTS 5,218,093 A * 6/1993 Guo et al. ............. 530/399
5,580,726 A   12/1996 Villeponteau et al.
(Continued)

FOREIGN PATENT DOCUMENTS

WO  WO 93/23550 A2  11/1993
WO  WO 95/25166 A1   9/1995
(Continued)

OTHER PUBLICATIONS

Extended European Search Report for Application No. 11760220.1 mailed Dec. 13, 2013.
(Continued)

*Primary Examiner* — Zachary Howard
(74) *Attorney, Agent, or Firm* — Wolf, Greenfield & Sacks, P.C.

(57) ABSTRACT

The invention provides methods and compositions for reducing, preventing or reversing cardio toxicity side effects associated with certain therapeutic agents. The invention also provides methods and compositions for treating heart dysfunction including heart failure, and for reversing the effects of myocardial infarction. The various aspects of the invention involve the use of ligand dimers, such as neuregulin dimers, that selectively induce the dimerization of certain EGF receptors in cardiac tissue.

12 Claims, 9 Drawing Sheets

(51) Int. Cl.
*A61K 38/18* (2006.01)
*A61K 38/17* (2006.01)
*C07K 14/475* (2006.01)
*C07K 14/485* (2006.01)
*C07K 19/00* (2006.01)

(56) References Cited

U.S. PATENT DOCUMENTS

| | | | |
|---|---|---|---|
| 5,763,584 | A | 6/1998 | Godowski |
| 6,004,555 | A | 12/1999 | Thorpe et al. |
| 6,127,337 | A | 10/2000 | Konishi et al. |
| 6,500,934 | B1 | 12/2002 | Lerner et al. |
| 6,635,249 | B1 | 10/2003 | Marchionni et al. |
| 2002/0002276 | A1 | 1/2002 | Fitzpatrick et al. |
| 2003/0087306 | A1 | 5/2003 | Christensen et al. |
| 2003/0186868 | A1 | 10/2003 | Rosenbaum et al. |
| 2003/0190702 | A1 | 10/2003 | Maihle et al. |
| 2003/0207391 | A1 | 11/2003 | Pappa |
| 2005/0036984 | A1 | 2/2005 | Harrison et al. |
| 2006/0019888 | A1 | 1/2006 | Zhou |
| 2006/0183194 | A1 | 8/2006 | Ballinger et al. |
| 2006/0183887 | A1 | 8/2006 | Jakobovits et al. |
| 2006/0228357 | A1 | 10/2006 | Chang et al. |
| 2007/0009972 | A1 | 1/2007 | Chao et al. |
| 2007/0092528 | A1 | 4/2007 | Sun |
| 2007/0117755 | A1 | 5/2007 | Liang |
| 2007/0154994 | A1 | 7/2007 | De Crescenzo et al. |
| 2007/0196379 | A1* | 8/2007 | Marchionni et al. ........ 424/158.1 |
| 2012/0040900 | A1* | 2/2012 | Alvarez et al. ................. 514/9.6 |

FOREIGN PATENT DOCUMENTS

| | | | |
|---|---|---|---|
| WO | WO 98/02540 A2 | 1/1998 |
| WO | 00/64400 A2 | 11/2000 |
| WO | WO 01/90192 A2 | 11/2001 |
| WO | WO 02/051869 A1 | 7/2002 |
| WO | WO 02/102854 A2 | 12/2002 |
| WO | WO 02/102972 A2 | 12/2002 |
| WO | WO 02/102973 A2 | 12/2002 |
| WO | WO 03/012045 A2 | 2/2003 |
| WO | WO 03/014159 A1 | 2/2003 |
| WO | WO 03/099300 A1 | 12/2003 |
| WO | WO 2004/087766 A2 | 10/2004 |
| WO | WO 2004/112717 A2 | 12/2004 |
| WO | WO 2007/046893 A2 | 4/2007 |
| WO | WO 2007/066106 A1 | 6/2007 |
| WO | WO 2007/066109 A1 | 6/2007 |
| WO | WO 2007/146959 A2 | 12/2007 |
| WO | WO 2008/140814 A1 | 11/2008 |
| WO | WO 2010/033249 A2 | 3/2010 |

OTHER PUBLICATIONS

Bian et al., Neuregulin-1 attenuated doxorubicin-induced decrease in cardiac troponins. Am J Physiol Heart Circ Physiol. Dec. 2009;297(6):H1974-83. Epub Oct. 2, 2009.
Montero et al., Neuregulins and cancer. Clin Cancer Res. Jun. 1, 2008;14(11):3237-41.
Xu et al., Neuregulin-1/ErbB signaling: a druggable target for treating heart failure. Curr Opin Pharmacol. Apr. 2009;9(2):214-9. Epub Dec. 11, 2008.
Invitation to Pay Additional Fees for Application No. PCT/US2011/029799 mailed Jun. 16, 2011.
International Search Report and Written Opinion for Application No. PCT/US2011/029799 mailed Aug. 18, 2011.
International Preliminary Report on Patentability for Application No. PCT/US2011/029799 mailed Oct. 4, 2012.
International Search Report and Written Opinion for Application No. PCT/US2009/005252 mailed Jun. 14, 2010.
International Preliminary Report on Patentability for Application No. PCT/US2009/005252 mailed Mar. 31, 2011.
Alvarez, Modulating Cell Behavior With Engineered Bivalent HER-Receptor Ligands. Thesis sumitted to the Department of Biological Engineering on Aug. 24, 2009 in Partial Fulfillment of the Requirements for the Degree of Doctor of Philosophy in Biological Engineering at Massachusetts Institute of Technology. 130 pages.
Arteaga et al., Unliganded epidermal growth factor receptor dimerization induced by direct interaction of quinazolines with the ATP binding site. J Biol Chem. Sep. 12, 1997;272(37):23247-54.
Bazley et al., The epidermal growth factor receptor family. Endocr Relat Cancer. Jul. 2005;12 Suppl 1:S17-27.
Bersell et al., Neuregulin1/ErbB4 signaling induces cardiomyocyte proliferation and repair of heart injury. Cell. Jul. 23, 2009;138(2):257-70. doi: 10.1016/j.cell.2009.04.060.
Bian et al, Neuregulin-1 attenuated doxorubicin-induced decrease in cardiac troponins. Am J Physiol Heart Circ Physiol. Dec. 2009;297(6):H1974-83. doi: 10.1152/ajpheart.01010.2008. Epub Oct. 2, 2009.
Chen et al., Transmembrane domain sequence requirements for activation of the p185c-neu receptor tyrosine kinase. J Cell Biol. May 5, 1997;137(3):619-31.
Comoglio et al., Interactions between growth factor receptors and adhesion molecules: breaking the rules. Curr Opin Cell Biol. Oct. 2003;15(5):565-71.
Crone et al., ErbB2 is essential in the prevention of dilated cardiomyopathy. Nat Med. May 2002;8(5):459-65.
Davis et al., Local myocardial insulin-like growth factor 1 (IGF-1) delivery with biotinylated peptide nanofibers improves cell therapy for myocardial infarction. Proc Natl Acad Sci U S A. May 23, 2006;103(21):8155-60. Epub May 12, 2006.
Fan et al., Antibody-induced epidermal growth factor receptor dimerization mediates inhibition of autocrine proliferation of A431 squamous carcinoma cells. J Biol Chem. Nov. 4, 1994;269(44):27595-602.
Fan et al., Regulation of epidermal growth factor receptor in NIH3T3/HER14 cells by antireceptor monoclonal antibodies. J Biol Chem. Oct. 5, 1993;268(28):21073-9.
Fan et al., Tethered epidermal growth factor provides a survival advantage to mesenchymal stem cells. Stem Cells. May 2007;25(5):1241-51. Epub Jan. 18, 2007.
Faress et al., Bleomycin-induced pulmonary fibrosis is attenuated by a monoclonal antibody targeting HER2. J Appl Physiol (1985). Dec. 2007;103(6):2077-83. Epub Oct. 4, 2007.
Ferguson et al., Ligand-induced conformational changes in the epidermal growth factor receptor. FASEB Journal. ASBMB Annual Meeting and 8$^{th}$ IUBMB Conference. Boston, Massachusetts. Jun. 12-16, 2004. Abstract 103.2, p. C228.
Fukazawa et al., Neuregulin-1 protects ventricular myocytes from anthracycline-induced apoptosis via erbB4-dependent activation of PI3-kinase/Akt. J Mol Cell Cardiol. Dec. 2003;35(12):1473-9.
Guillemard et al., HER2-mediated internalization of a targeted prodrug cytotoxic conjugate is dependent on the valency of the targeting ligand. DNA Cell Biol. Jun. 2005;24(6):350-8.
Hsieh et al., Controlled delivery of PDGF-BB for myocardial protection using injectable self-assembling peptide nanofibers. J Clin Invest. Jan. 2006;116(1):237-48. Epub Dec. 15, 2005.
Hsieh et al., Local controlled intramyocardial delivery of platelet-derived growth factor improves postinfarction ventricular function without pulmonary toxicity. Circulation. Aug. 15, 2006;114(7):637-44. Epub Aug. 7, 2006.
Hynes, Integrins: bidirectional, allosteric signaling machines. Cell. Sep. 20, 2002;110(6):673-87.
Jay et al., An engineered bivalent neuregulin protects against doxorubicin-induced cardiotoxicity with reduced proneoplastic potential. Circulation. Jul. 9, 2013;128(2):152-61. Doi:10.1161/CIRCULATIONAHA.113.002203. Epub Jun. 11, 2013.
Jay et al., Engineered bivalent ligands to bias ErbB receptor-mediated signaling and phenotypes. J Biol Chem. Aug. 5, 2011;286(31):27729-40. Doi: 10.1074/jbc.M111.221093. Epub May 26, 2011.
Jay et al., Supplemental Data to Engineered bivalent ligands to bias ErbB receptor-mediated signaling and phenotypes. J Biol Chem. Aug. 5, 2011;286(31):27729-40. Doi: 10.1074/jbc.M111.221093. Epub May 26, 2011.
Jones et al., Binding specificities and affinities of egf domains for ErbB receptors. FEBS Lett. Mar. 26, 1999;447(2-3):227-31.

(56) References Cited

OTHER PUBLICATIONS

Knowlden et al., Elevated levels of epidermal growth factor receptor/c-erbB2 heterodimers mediate an autocrine growth regulatory pathway in tamoxifen-resistant MCF-7 cells. Endocrinology. Mar. 2003;144(3):1032-44.

Kühn et al., Periostin induces proliferation of differentiated cardiomyocytes and promotes cardiac repair. Nat Med. Aug. 2007;13(8):962-9. Epub Jul. 15, 2007.

Kumagai et al., Role of extracellular subdomains of p185c-neu and the epidermal growth factor receptor in ligand-independent association and transactivation. Proc Natl Acad Sci U S A. Aug. 5, 2003;100(16):9220-5. Epub Jul. 16, 2003.

Kuramochi et al., Neuregulin activates erbB2-dependent src/FAK signaling and cytoskeletal remodeling in isolated adult rat cardiac myocytes. J Mol Cell Cardiol. Aug. 2006;41(2):228-35.

Langenickel et al., Forced homodimerization by site-directed mutagenesis alters guanylyl cyclase activity of natriuretic peptide receptor B. Hypertension. Feb. 2004;43(2):460-5. Epub Dec. 22, 2003.

Liotta et al., Cancer metastasis and angiogenesis: an imbalance of positive and negative regulation. Cell. Jan. 25, 1991;64(2):327-36.

Liu et al., Neuregulin-1/erbB-activation improves cardiac function and survival in models of ischemic, dilated, and viral cardiomyopathy. J Am Coll Cardiol. Oct. 3, 2006;48(7):1438-47. Epub Sep. 14, 2006.

Maradia et al., Pharmacologic prevention of anthracycline-induced cardiomyopathy. Cardiol Rev. Sep.-Oct. 2009;17(5):243-52. doi: 10.1097/CRD.0b013e3181b8e4c8. Erratum in Cardiol Rev. Nov.-Dec. 2009;17(6):299.

Martin et al., Rebuilt AAA + motors reveal operating principles for ATP-fuelled machines. Nature. Oct. 20, 2005;437(7062):1115-20.

Menendez et al., Targeting human epidermal growth factor receptor 2: it is time to kill kinase death human epidermal growth factor receptor 3. J Clin Oncol. Jun. 10, 2007;25(17):2496-8; author reply 2499.

Moll et al., Designed heterodimerizing leucine zippers with a ranger of pIs and stabilities up to 10(-15) M. Protein Sci. Mar. 2001;10(3):649-55.

Muthuswamy et al., ErbB2, but not ErbB1, reinitiates proliferation and induces luminal repopulation in epithelial acini. Nat Cell Biol. Sep. 2001;3(9):785-92.

Muthuswamy et al, Controlled dimerization of ErbB receptors provides evidence for differential signaling by homo- and heterodimers. Mol Cell Biol. Oct. 1999;19(10):6845-57.

Nakaji-Hirabayashi et al., Surface-anchoring of spontaneously dimerized epidermal growth factor for highly selective expansion of neural stem cells. Bioconjug Chem. Jan. 2009;20(1):102-10. Doi: 10.1021/bc800331t.

Ogiso et al., Crystal structure of the complex of human epidermal growth factor and receptor extracellular domains. Cell. Sep. 20, 2002;110(6):775-87.

Otto et al., Cell proliferation through forced engagement of c-Kit and Flt-3. Blood. Jun. 1, 2001;97(11):3662-4.

Park et al., PEGylated PLGA nanoparticles for the improved delivery of doxorubicin. Nanomedicine. Dec. 2009;5(4):410-8. doi: 10.1016/j.nano.2009.02.002. Epub Mar. 31, 2009.

Qazi et al., Ligand-independent homo- and heterodimerization of human prolactin receptor variants: inhibitory action of the short forms by heterodimerization. Mol Endocrinol. Aug. 2006;20(8):1912-23. Epub Mar. 23, 2006.

Rahman et al., Doxorubicin-induced chronic cardiotoxicity and its protection by liposomal administration. Cancer Res. May 1982;42(5):1817-25.

Rayson et al., Anthracycline-trastuzumab regimens for HER2/neu-overexpressing breast cancer: current experience and future strategies. Ann Oncol. Sep. 2008;19(9):1530-9. doi: 10.1093/annonc/mdn292. Epub May 13, 2008.

Sawyer et al., Modulation of anthracycline-induced myofibrillar disarray in rat ventricular myocytes by neuregulin-1beta and anti-erbB2: potential mechanism for trastuzumab-induced cardiotoxicity. Circulation. Apr. 2, 2002;105(13):1551-4.

Segers et al., Local delivery of protease-resistant stromal cell derived factor-1 for stem cell recruitment after myocardial infarction. Circulation. Oct. 9, 2007;116(15):1683-92. Epub Sep. 17, 2007.

Shi et al., Study of inhibition effect of erceptin on interaction between heregulin and erbB receptors HER3/HER2 by single-molecule force spectroscopy. Exp Cell Res. Oct. 1, 2009;315(16):2847-55. Doi: 10.1016/j.yexcr.2009.05.023. Epub Jun. 1, 2009.

Spaargaren et al., Antibody-induced dimerization activates the epidermal growth factor receptor tyrosine kinase. J Biol Chem. Jan. 25, 1991;266(3):1733-9.

Sternsdorf et al., Forced retinoic acid receptor alpha homodimers prime mice for APL-like leukemia. Cancer Cell. Feb. 2006;9(2):81-94.

Stuhlmann-Laeisz et al., Forced dimerization of gp130 leads to constitutive STAT3 activation, cytokine-independent growth, and blockade of differentiation of embryonic stem cells. Mol Biol Cell. Jul. 2006;17(7):2986-95. Epub Apr. 19, 2006.

Surette et al., Role of alpha-helical coiled-coil interactions in receptor dimerization, signaling, and adaptation during bacterial chemotaxis. J Biol Chem. Jul. 26, 1996;271(30):17966-73.

Tamama et al., Epidermal growth factor as a candidate for ex vivo expansion of bone marrow-derived mesenchymal stem cells. Stem Cells. Mar. 2006;24(3):686-95. Epub Sep. 8, 2005.

Tzahar et al., Bivalence of EGF-like ligands drives the ErbB signaling network. EMBO J. Aug. 15, 1997; 16(16): 4938-4950. doi: 10.1093/emboj/16.16.

Wiley, Trafficking of the ErbB receptors and its influence on signaling. Exp Cell Res. Mar. 10, 2003;284(1):78-88.

Witton et al., Expression of the HER1-4 family of receptor tyrosine kinases in breast cancer. J Pathol. Jul. 2003;200(3):290-7.

Wouters et al., Protecting against anthracycline-induced myocardial damage: a review of the most promising strategies. Br J Haematol. Dec. 2005;131(5):561-78.

Yarden et al., Untangling the ErbB signalling network. Nat Rev Mol Cell Biol. Feb. 2001;2(2):127-37.

Zaczek et al., The diverse signaling network of EGFR, HER2, HER3 and HER4 tyrosine kinase receptors and the consequences for therapeutic approaches. Histol Histopathol. Jul. 2005;20(3):1005-15.

Zhan et al., Controlled activation of ErbB1/ErbB2 heterodimers promote invasion of three-dimensional organized epithelia in an ErbB1-dependent manner: implications for progression of ErbB2-overexpressing tumors. Cancer Res. May 15, 2006;66(10):5201-8.

\* cited by examiner

SEQUENCE LISTING

```
<160> NUMBER OF SEQ ID NOS: 5

<210> SEQ ID NO 1
<211> LENGTH: 47
<212> TYPE: PRT
<213> ORGANISM: Artificial Sequence
<220> FEATURE:
<223> OTHER INFORMATION: Synthetic peptide

<400> SEQUENCE: 1

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Pro Leu Gly Gly Gly Lys
        35                  40                  45

<210> SEQ ID NO 2
<211> LENGTH: 47
<212> TYPE: PRT
<213> ORGANISM: Artificial Sequence
<220> FEATURE:
<223> OTHER INFORMATION: Synthetic peptide

<400> SEQUENCE: 2

Lys Gly Gly Gly Leu Glu Ile Arg Ala Ala Phe Leu Arg Arg Arg Asn
1               5                   10                  15

Thr Ala Leu Arg Thr Arg Val Ala Glu Leu Arg Gln Arg Val Gln Arg
            20                  25                  30

Leu Arg Asn Ile Val Ser Gln Tyr Glu Thr Arg Tyr Gly Pro Leu
        35                  40                  45

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 3

Lys Pro Val Ser Leu Ser Tyr Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ser Lys Pro Val Ser Leu Ser Tyr Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Ser Lys Pro Val Val Leu Ser Tyr Arg
1               5
```

METHODS FOR CARDIOPROTECTION AND CARDIOREGENERATION WITH DIMERS OF EGF FAMILY LIGANDS

RELATED APPLICATIONS

This application is a national stage filing under 35 U.S.C. §371 of international PCT application number, PCT/US2011/029799, filed on Mar. 24, 2011, which claims the benefit under 35 U.S.C §119(e) of U.S. provisional application Ser. No. U.S. 61/317,094, entitled "METHODS AND COMPOSITIONS FOR CARDIOPROTECTION AND CARDIOREGENERATION," filed on Mar. 24, 2010, the disclosure of each of which is incorporated by reference herein in its entirety.

GOVERNMENT SUPPORT

This invention was made with government support under Grant Nos. EB003805 and DE019523 awarded by the National Institutes of Health and under Contract No. W81XWH-08-2-0034 awarded by the U.S. Army Medical Research and Material Command. The government has certain rights in the invention.

FIELD OF THE INVENTION

The invention provides methods and compositions for cardioprotection and cardiac regeneration using ligands from the epidermal growth factor (EGF) family.

SUMMARY OF THE INVENTION

In its broadest sense, the invention relates to the use of ligands in the epidermal growth factor (EGF) family in cardioprotective and cardioregenerative methods.

More specifically, in some aspects, the invention contemplates methods for preventing or reducing cardiotoxicity associated with the use of certain therapeutic agents. An example of such therapeutic agents is the anthracyclines, a specific example of which is doxorubin. The invention further contemplates methods for increasing the amount and/or frequency of, for example, anthracycline therapy without a concomitant increase in cardiotoxicity. In certain instances, the invention provides methods for modulating cardiotoxicity in real-time (i.e., as it is occurring) or for reversing cardiotoxic effects that occurred previously.

In other aspects, the invention contemplates methods for preventing or treating cardiac dysfunction and/or reducing or reversing the effects of cardiac insult that arises independently of cardiotoxicity-associated therapeutic agents. Cardiac dysfunction may embrace a chronic condition such as heart failure and more specifically congestive heart failure, or it may embrace an acute condition such as a myocardial infarction. Myocardial damage may be reduced or reversed in subjects by treatment with ligands from the EGF family of ligands, including ligand dimers.

The methods of the invention employ, in some instances, ligand monomers and, in other instances, ligand dimers. The dimers may be homodimers such as neuregulin homodimers (referred to herein interchangeably as neuregulin dimers), e.g., neuregulin-1B homodimers, spitz homodimers (referred to herein interchangeably as spitz dimers), or EGF homodimers (referred to herein interchangeably as EGF dimers). Alternatively, the dimers may be heterodimers such as dimers that comprise any two of a neuregulin ligand, a spitz ligand and an EGF ligand. Examples of heterodimers contemplated by the invention are dimers comprising a neuregulin ligand and an EGF ligand, dimers comprising a neuregulin ligand and a spitz ligand, and dimers comprising an EGF ligand and a spitz ligand. In some important embodiments, the dimer is a neuregulin homodimer.

Thus, in one aspect, the invention provides a method for reducing anthracycline-associated cardiotoxicity comprising administering to a subject, in need of anthracycline therapy, a ligand dimer in an amount effective to reduce anthracycline-associated cardiotoxicity. In some embodiments, the subject is administered an amount of anthracycline therapy above the normally administered amount.

In another aspect, the invention provides a method for increasing anthracycline tolerable dose comprising administering to a subject, in need of anthracycline therapy, a ligand dimer and an anthracycline, wherein the anthracycline is administered in an amount above the normally administered amount.

In some embodiments, the tolerable dose is a dose per administration. In some embodiments, the tolerable dose is cumulative dose.

In some embodiments, the anthracycline therapy is administered in an amount that is about 10% above the normally administered amount. In some embodiments, the anthracycline therapy is administered in an amount that is about 25% above the normally administered amount.

In some embodiments, the anthracycline therapy is doxorubicin.

In some embodiments, the subject is administered the ligand dimer prior to the anthracycline therapy. In some embodiments, the subject is administered the ligand dimer after the anthracycline therapy. In some embodiments, the subject is administered the ligand dimer prior and during (i.e., substantially simultaneously with) the anthracycline therapy, or prior to and after the anthracycline therapy, or during and after the anthracycline therapy, or prior to, during and after the anthracycline therapy.

In some embodiments, the ligand dimer is administered locally to the heart. In some embodiments, the ligand dimer is administered systemically. In some embodiments, the ligand dimer is administered in a sustained release formulation. In some embodiments, the anthracycline therapy is administered locally. In some embodiments, the anthracycline therapy is administered systemically. In some embodiments, the anthracycline therapy is administered systemically and the ligand dimer is administered locally to the heart.

In another aspect, the invention provides a method for reducing anthracycline-associated cardiotoxicity comprising administering to a subject, that has been administered an anthracycline, a ligand dimer in an amount effective to reduce anthracycline-associated cardiotoxicity. In some embodiments, the ligand dimer is administered days, weeks, months, or even years after the last anthracycline administration (sometime referred to herein as the cessation of anthracycline therapy). As an example, the ligand dimer may be administered at least 1 week after the last anthracycline administration, at least 2 weeks, at least 3 weeks, at least 4 weeks, at least 2 months, at least 3 months, at least 4 months, at least 5 months, at least 6 months, at least 1 year, at least 2 years, at least 3 years, at least 4 years, at least 5 years, or longer after the last anthracycline administration. In some embodiments, the anthracycline therapy is doxorubicin.

The invention, in still another aspect, contemplates treating a subject that has been exposed, is being exposed, and/or is likely to be exposed to an agent that is associated with cardiotoxicity by administering to the subject a ligand dimer of the invention in an amount effective to prevent or reduce cardiotoxicity.

In still another aspect, the invention provides a method for treating a subject comprising administering to a subject, that is experiencing or has experienced a myocardial infarction, a ligand dimer in an amount effective to reduce infarct size. In some embodiments, the ligand dimer is administered locally to the heart. In some embodiments, the ligand dimer is administered in a sustained delivery formulation. In some embodiments, the subject has experienced a myocardial infarction. In some embodiments, the subject is experiencing a myocardial infarction. In some embodiments, the subject may or may not have coronary artery disease. In some embodiments, the subject may or may not have atherogenesis of the coronary arteries.

In another aspect, the invention provides a method for treating a subject comprising administering to a subject having heart failure a ligand dimer in an amount effective to treat the subject. In some embodiments, the ligand dimer is administered locally to the heart. In some embodiments, the ligand dimer is administered in a sustained delivery formulation. In some embodiments, the subject may or may not have coronary artery disease. In some embodiments, the subject may or may not have atherogenesis of the coronary arteries.

In any one of the foregoing aspects or embodiments, the ligand dimer is an NRG homodimer. In any one of the foregoing aspects or embodiments, the ligand dimer is an EGF homodimer. In any one of the foregoing aspects or embodiments, the ligand dimer is a spitz homodimer.

In any one of the foregoing aspects or embodiments, the ligand dimer comprises an epidermal growth factor (EGF) ligand, a neuregulin ligand, and/or a spitz ligand. As used herein, a ligand dimer that comprises an epidermal growth factor (EGF) ligand, a neuregulin ligand, and/or a spitz ligand is a ligand dimer that comprises at least one of an EGF ligand, an neuregulin ligand, or a spitz ligand. The ligand dimer may be a homodimer of any of these, or it may be a heterodimer that comprises any two of an EGF ligand, an NRG ligand and spitz. In any one of the foregoing aspects or embodiments, the ligand dimer comprises a neuregulin ligand and an EGF ligand. In any one of the foregoing aspects or embodiments, the ligand dimer comprises a spitz ligand and a neuregulin ligand. In any one of the foregoing aspects or embodiments, the ligand dimer comprises a spitz ligand and an EGF ligand.

In any one of the foregoing aspects or embodiments, the ligand dimer is a neuregulin-1β homodimer or a heterodimer comprising a neuregulin-1β ligand. In any one of the foregoing aspects or embodiments, the ligand dimer is a neuregulin-3 homodimer or a heterodimer comprising a neuregulin-3 ligand. In any one of the foregoing aspects or embodiments, the ligand dimer is a neuregulin-4 homodimer or a heterodimer comprising a neuregulin-4 ligand. In any one of the foregoing aspects or embodiments, the ligand dimer is a ligand dimer that dimerizes HER1 and HER1, or that dimerizes HER4 and HER4, or that dimerizes HER1 and HER2, or that dimerizes HER1 and HER4, or that dimerizes HER2 and HER4, or that dimerizes HER3 and HER3. In any one of the foregoing aspects or embodiments, the ligand dimer is a ligand dimer that dimerizes, oligomerizes, or aggregates any of the foregoing HER receptors.

In any of the foregoing aspects and embodiments, the amount of ligand dimer that is administered to a subject may be less than the amount of ligand monomer (or combination of ligand monomers) that would have to be administered to achieve the same effect. In some embodiments, the same therapeutic effects may never be achieved when using ligand monomers, as compared to ligand dimers.

In yet another aspect, the invention provides a ligand dimer, comprising two ligands, at least one of which is a spitz ligand, and a linker, wherein the ligand dimer causes dimerization of receptors at least one of which is a HER receptor.

In some embodiments, each of the two ligands is a spitz ligand. In some embodiments, one of the two ligands is an integrin ligand, and wherein the ligand dimer causes dimerization of one or more specific Her-integrin receptor pairs. In some embodiments, one of the ligands is a HER1 ligand that is not spitz. In some embodiments, one of the ligands is a HER4 ligand. In some embodiments, the HER4 ligand is neuregulin-1β.

In some embodiments, the linker comprises a coiled coil domain. In some embodiments, the linker further comprises peptide spacers.

In some embodiments, peptide spacer is a 20 amino acid peptide. In some embodiments, the linker comprises a water soluble flexible polymer. In some embodiments, the water soluble flexible polymer is polyethylene oxide (PEO), dextran, polyacrylic acid, or polyacrylamide.

In yet still another aspect, the invention provides a composition comprising the ligand dimer comprising two ligands, at least one of which is a spitz ligand, and a linker, wherein the ligand dimer causes dimerization of receptors at least one of which is a HER receptor, wherein the ligand dimer is attached to a substrate.

In some embodiments, the substrate is an extracellular matrix. In some embodiments, the substrate is a tissue engineering scaffold.

In still another aspect, the invention provides a ligand dimer, comprising two ligands, wherein the ligand dimer causes dimerization, oligomerization, or aggregation of receptors at least one of which is a HER receptor. In one embodiment, the ligand dimer comprises at least one neuregulin-1β ligand. In another embodiment, the HER receptor is a HER3 receptor.

In some embodiments, the invention provides a ligand dimer, e.g., a NRG homodimer (NN)), wherein the ligand dimer causes dimerization, oligomerization, or aggregation of HER3 receptors, thereby inhibiting (reducing or eliminating) phosphorylation by the HER3 receptor. In other embodiments, the ligand dimer prevents dimerization, oligomerization, or aggregation of HER2 and HER3 receptors. In some of these embodiments, the prevention of the dimerization, oligomerization, or aggregation of HER2 and HER3 receptors results in the dimerization, oligomerization, or aggregation of HER3 receptors and an inhibition of signaling.

In one aspect, the invention provides a method of controlling HER dimerization/oligomerization/aggregation, wherein a ligand dimer is used in an effective amount such that the ratio of ligand or ligand dimer:HER receptor is 1, 1.5, 2, 2.5, 3, 4, 5, 6, 7, 8, 9, 10 or more (on average) when the ligand or ligand dimer is in contact with or in the vicinity of (i.e., can come into contact with one or more receptors on the cell surface) the surface of one or more cells. In some embodiments, the ratio of ligand or ligand dimer to HER receptor is less than or equal to 3. In other embodiments, the ratio of ligand or ligand dimer to HER receptor is less than 3.

These and other aspects and embodiments of the invention will be described in greater detail herein.

Each of the limitations of the invention can encompass various embodiments of the invention. It is therefore anticipated, unless otherwise stated, that each of the limitations of the invention involving any one element or combinations of elements can be included in each aspect of the invention. This invention is not limited in its application to the details of construction and/or the arrangement of components set forth in the following description or illustrated in the figures. The invention is capable of other embodiments and of being practiced or of being carried out in various ways, as will be apparent to those of ordinary skill based on the teachings provided herein.

BRIEF DESCRIPTION OF THE FIGURES

The accompanying figures are not intended to be drawn to scale. In the figures, each identical or nearly identical component that is illustrated in various figures is represented by a like numeral. For purposes of clarity, not every component may be labeled in every figure.

DETAILED DESCRIPTION OF THE INVENTION

Figure 1A:
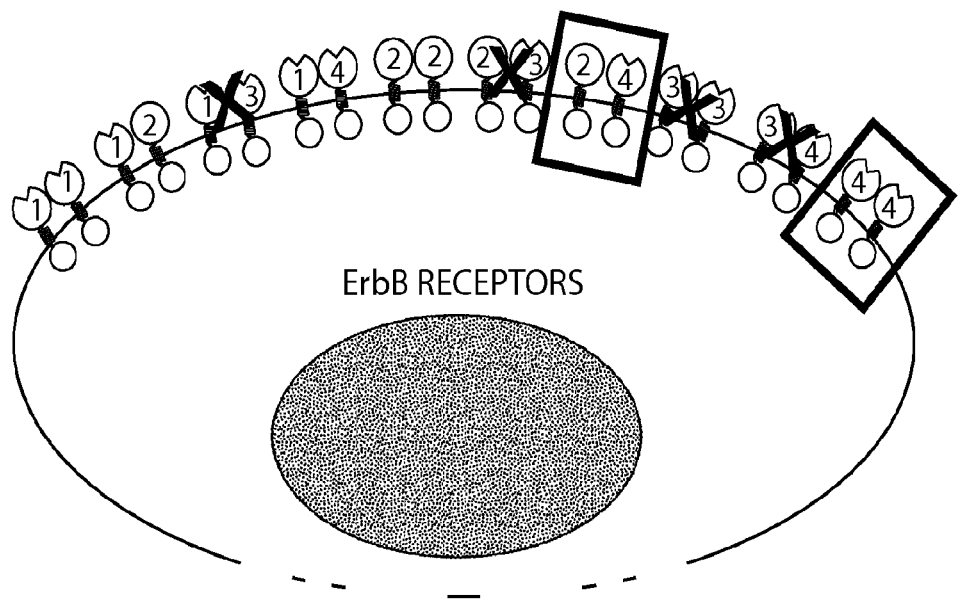
FIGS. 1A and B. Neuregulin/ErbB signaling axis in cardiomyocytes. (A) ErbB receptors on cardiomyocytes can form 6 potential dimer pairs. ErbB3 is not expressed on postnatal cardiomyocytes. NRG, via its high affinity for ErbB4, signals primarily through two different dimer pairs, ErbB2/ErbB4 heterodimers and ErbB4/ErbB4 homodimers. (B) Formation of these dimer pairs leads to distinct downstream cellular effects.
Figure 1B:
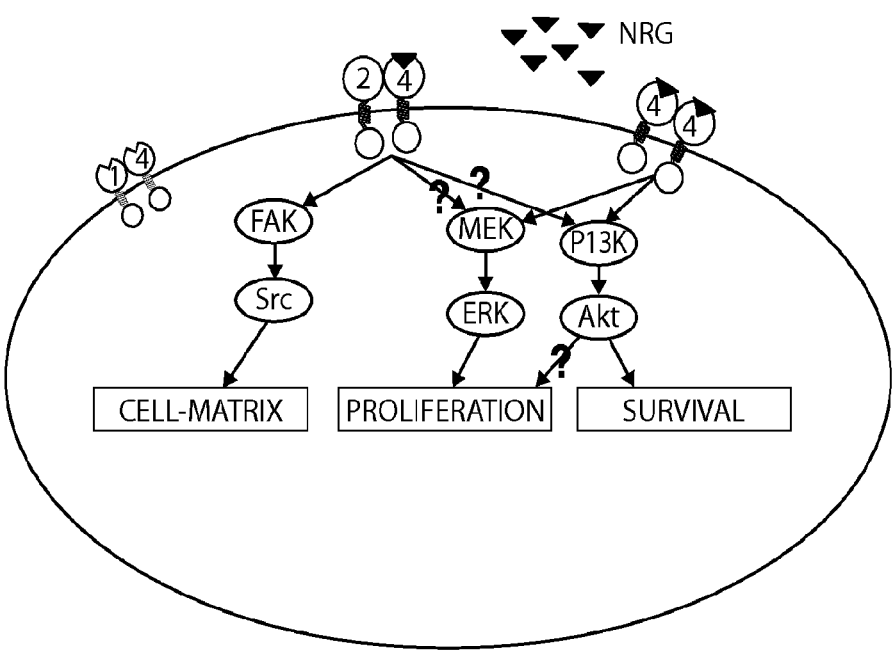

The invention relates to the use of ligands for the ErbB/ HER family of receptors in methods for protecting cardiac tissue from damage, limiting the extent of cardiac damage and/or reversing existing cardiac damage. The ligands may be used in monomeric form although in some instances dimeric forms are preferred as they provide unexpected and thus surprising results, potentially because they may be able to initiate distinct signaling pathways as compared to the monomeric ligands, thereby leading to different functional outcomes. To this end, the methods provided herein have broad application and can be used for subjects having cardiac damage (and resulting dysfunction) as well as those likely to experience cardiac damage. Although not intending to be bound any particular mechanism, the ligand compositions of the invention may exert their effects by inducing regeneration of cardiac tissue or by protecting cardiac tissue from damage or death. Thus, the methods of the invention may be considered to be cardioprotective and/or cardioregenerative. Some methods of the invention are therefore useful in the treatment of at least the estimated 5,700,000 Americans afflicted with heart failure.

The invention is based, at least in part, on the unexpected finding that certain ligand dimers are able to limit and/or reverse cardiotoxicity associated with certain therapeutic agents. In particular, as shown in the Examples, cardiotoxicity associated with the anthracycline class of therapeutic agents can be reduced in whole or in part through the use of neuregulin-1β (NRG1) dimers. Other ErbB receptor ligands, including other neuregulin isoforms, may be use to reduce cardiotoxicity associated with anthracyclines. Anthracyclines are used extensively in the treatment of various cancers yet their efficacy is limited by their side effects. One such side effect is cardiotoxicity. The invention therefore provides methods for increasing the efficacy of anthracyclines by reducing or preventing their cardiotoxic side effects. In some embodiments, this is accomplished simply by reducing the incidence and/or severity of cardiotoxic side effects associated with anthracyclines. In some embodiments, this is accomplished by administering a higher dose and/or overall amount of an anthracycline than would otherwise be tolerated. In still other embodiments, this is accomplished by administering an anthracycline more regularly than would otherwise be possible. In some embodiments of the invention, the ligand dimer, and in particular the NRG ligand dimer, is administered via intracoronary infusion or directly to the heart while the anthracycline may be administered systemically.

As a specific example of the applicability of some aspects of the invention, doxorubicin, an anthracycline drug, is among the most effective anti-cancer therapeutics ever developed, and it has efficacy in a variety of malignancies in adults and children. However, clinical use of this agent is limited by its dose-dependent cardiotoxicity, which can lead to cardiomyopathy and heart failure. The ability to limit doxorubicin-induced cardiotoxicity provided by the methods of the invention allows higher, longer and/or more frequent doxorubicin dosing regimens, thereby increasing the antitumor potency and efficacy of this drug. Some methods of the invention are therefore useful in the treatment of the expected approximately 192,000 new cases of breast cancer that are diagnosed every year, as well for subjects already being treated for breast cancer using these cardiotoxicity-associated therapeutic agents.

Receptors in the ErbB/HER family require receptor dimerization induced by ligand binding in order to signal, and receptors can homodimerize or heterodimerize with other members of the family as well as with other receptors, such as the integrins. The ErbB/HER receptor family members activate multiple intracellular signaling pathways including ERK, PLC$\gamma$, and PI3kinase/Akt. These pathways influence cell survival, migration, proliferation, and differentiation.

Thus, although not intending to be bound by any particular mechanism, the ligand dimers are thought to exert their effects through selective, pre-determined (or forced) dimerization, oligomerization, and/or aggregation, leading to specific activation and signal transduction of certain receptors. This in turn reduces (and in some cases excludes altogether) the likelihood that other receptors dimerize and transduce signal. If an ErbB/HER receptor is not able to dimerize, normally it does not become activated and does not transduce signal intracellularly. Through the use of ligand dimers, it is possible to control which ErbB/HER receptors are more likely to interact and transduce signal, and conversely which receptors are less likely to dimerize and transduce signal.

Known natural ligands of the ErbB/HER receptors are monomeric. Efforts to stimulate these receptors to date have employed monomeric soluble ligands and such ligands are commercially available from many sources. Efforts to inhibit signaling have focused on small molecule inhibitors of kinases, on antibodies that block ligand binding, or antibodies that sterically inhibit dimerization.

The invention, on the other hand, is based in part on the recognition that the ErbB/HER signaling can be modulated using ErbB/HER ligand dimers. These ligand dimers are not known to be naturally occurring and, as a result, are referred to herein as being synthetic or engineered. As discussed herein, ligand dimers (or bivalent ligands as they are interchangeably referred to herein) are capable of biasing receptor dimerization/oligomerization/aggregation, which in turn directs downstream cell signaling effects and outcomes. In some instances, engineered bivalent ligands, but not native monomeric ligands, can effect and/or modulate cellular responses resulting in therapeutic cardiac benefit. As an example, it has been found, unexpectedly, that bivalent NRG provides superior cardioprotection to doxorubicin-associated cardiotoxicity as compared to native, monomeric NRG. The invention similarly contemplates that bivalent NRG is more effective in treating cardiac dysfunction than monovalent NRG.

The ligand dimers of the invention are used to effect and/or modulate interactions between the tyrosine kinase-class ErbB receptors (also known as HER receptors). This family of receptors is comprised of ErbB1 (also known as HER1 or EGFR), ErbB2 (also known as HER2), ErbB3 (also known as HER3), and ErbB4 (also known as HER4). There are twelve known ligands for this receptor family, each with different affinity for the various receptor family members. Significantly, there is no known ligand for ErbB2 (HER2). The variety of ligands facilitates formation of at least ten possible receptor dimer pairs.

Dimerization is essential for signaling from ErbB receptors, and each dimer pair is capable of initiating signaling cascades leading to distinct downstream effects. Because receptor dimerization is required to initiate signaling from these tyrosine kinases, and because of the diversity of ligand affinities for particular receptors in the family, the potential to bias signaling via forced ligand-receptor and receptor-receptor interactions exists.

Accordingly, it has been surprisingly found that signaling by ErbB family members can be controlled by forcing particular receptors to homo- or hetero-dimerize or oligomerize/aggregate, thereby increasing or decreasing signaling by quantitative control of receptor occupancy with select dimers. With monovalent ligands, each ligand-bound receptor is a "free agent" and can heterodimerize with any other ErbB family member and the absolute or relative number of each type of dimer is difficult to control. With ligand dimers, however, it has been found that it is possible to force receptors to dimerize/oligomerize/aggregate in a pre-determined and selective manner. For example, if a particular cell expresses 20,000 HER1 and 10,000 HER3, a soluble HER1 ligand dimer would lead to the homodimerization of HER1 and would tend to inhibit the dimerization of HER1 with HER3. Likewise a soluble EGF-NRG1 heterodimer ligand would drive most HER3 into heterodimers with HER1 and prevent dimerzation of HER3 with HER2. NRG1 dimers would drive HER3 homodimerization and/or HER4 homodimerization but would inhibit other dimer forms.

As will be clear to those of ordinary skill, the receptor dimers that are achieved on any given cell will depend in part on the nature and amount of ligand dimers used, the relative amount and type of naturally occurring monomers, and the types and amounts of each receptor expressed on the cell. When used in sufficient or effective amounts, the ligand dimers allow quantitative control over the nature and ratio of various activated (or silenced) receptor dimers, regardless of the total or relative expression levels of each type of receptor.

Provided herein, therefore, are compositions and methods for controlling homo- and hetero-dimerization/oligomerization/aggregation of the EGF/HER/ErbB (or EGF/HER/ErbB receptors, as the terms are used interchangeably). The dimers provided by the invention can be used to dimerize the wild type versions of these receptors as well as polymorphic or mutant versions of these receptors. As used herein, "controlling HER dimerization" refers to the ability to force (i.e., cause) the dimerization/oligomerization/aggregation of a HER receptor with an identical or a different HER receptor (i.e., dimerization of two receptors to form a receptor pair). The ability to control (or modulate) the nature and degree of HER receptor dimerization allows one to control (or modulate) signaling from these various receptors and receptor dimers. As used herein, "controlling HER oligomerization" refers to the ability to force the oligomerization of a HER receptor with one or more identical or different HER receptors. As used herein, "controlling HER aggregation" refers to the ability to force two or more identical or different HER receptors to aggregate together.

As shown in FIG. 1A, mature cardiomyocytes express, albeit to varying degrees, HER1, HER2 and HER4 but not HER3. Accordingly, the receptor dimers that may be formed include HER1 homodimers, HER2 homodimers, HER4 homodimers, HER1-HER2 heterodimers, HER1-HER4 heterodimers, and HER2-HER4 heterodimers.

Accordingly, in the context of cardiomyocytes, receptor signaling bias can be achieved, for example, through use of a ligand with high affinity for HER4/ErbB4. One such ligand is neuregulin-1β (NRG or NRG1, as used herein). To this end, the invention provides an NRG ligand homodimer. This homodimer induces HER4 homodimerization due to the high affinity of NRG for HER4/ErbB4. NRG binds HER3 and HER4 receptors with approximately 5000-fold greater affinity than HER1. ErbB3 is not expressed on cardiomyocytes however so exposure of these cells to an NRG dimer will stimulate the dimerization of HER4 homodimers without interference from HER3 receptors.

ErbB4-ErbB4 dimer formation can lead to induction of the PI3 kinase signaling cascade, a canonical cell survival pathway. PI3 kinase mediated cell survival is important in the response of cardiomyocytes to a toxic stimulus, such as that resulting from administration of doxorubicin, or other anthracycline drugs, to cancer patients. While doxorubicin is a highly effective anti-cancer agent, its total dose is limited by cardiotoxic side effects. Inducing cardiomyocyte survival in the presence of doxorubicin would, in some instances, enable higher doses of this drug to be administered to patients, increasing cancer cure rates and improving the quality of life for cancer survivors. A proof of principle that administration of bivalent NRG can reduce the toxic effects of doxorubicin on cardiomyocytes is provided herein. Moreover, by biasing signaling with the bivalent NRG to form more ErbB4-ErbB4 dimers than would normally be produced by administration of native NRG, which acts through both ErbB2-ErbB4 dimers and ErbB4-ErbB4 dimers, cardioprotection is dramatically increased as compared to the monovalent NRG as shown in FIGS. 2A and B.

Additionally, bivalent NRG does not require activation of the ErbB2 receptor for its beneficial effects. Since clinicians are employing regimens combining doxorubicin or other anthracyclines with antibodies against ErbB2 such as trastuzumab (Herceptin) to treat patients with invasive breast cancer marked by an overexpression of ErbB2, bivalent NRG could be used where native NRG would be expected to be even less effective.

Therapeutic Agents Associated with Cardiotoxicity

It is to be understood that while some aspects of the invention are described in terms of anthracyclines, the methods of the invention are broader and can be used with other therapeutic agents that are associated with cardiotoxicity. A therapeutic agent associated with cardiotoxicity is a therapeutic agent known or shown to induce cardiotoxicity. Such cardiotoxicity is typically a dose-limiting adverse side effect. The invention reduces the degree of cardiotoxicity induced by such agents and/or allows for increased amounts of agent to be administered to a subject without concomitantly increasing the degree of cardiotoxicity.

An important class of therapeutic agents associated with cardiotoxicity is the anthracyclines. Anthracyclines are agents that intercalate into DNA and inhibit topoisomerase II. Examples of anthracyclines are known in the art and include without limitation doxorubicin (also known as Adriamycin) and daunorubicin (also referred to as Daunomycin), epirubcin, idarubicin, valrubicin, and mitoxantrone. Because of their ability to kill bacteria as well as human cells, they are sometimes referred to as anthracycline antibiotics.

Anthracyclines are a sub-group of therapeutic agents referred to as anthracenediones. This broader class of agents is also associated with cardiotoxicity. Examples of anthracenediones include mitoxantrone (sometimes also considered an anthracycline) and pixantrone.

Some of these agents are formulated in liposomal form. The invention contemplates, in some instances, the use of liposomal forms of an anthracycline such as doxorubin or daunorubicin with the ligand dimers of the invention, since these liposomal forms are themselves less cardiotoxic.

Anthracyclines are used to treat a variety of cancers including leukemias, lymphomas, breast, uterine, ovarian, lung and bladder cancers. Accordingly, some aspects of the invention are methods for treating subjects having a condition that calls for treatment with an anthracycline (including any of the foregoing cancers), methods for increasing the efficacy of the anthracycline therapy, and/or methods for reducing cardiotoxicity in such subjects.

Numerous strategies for preventing DOX-induced cardiotoxicity have been explored, including limiting total dose, liposomal delivery, and pharmacologic prevention [1]. Reducing the cumulative dose of DOX is the standard approach to reducing cardiotoxic side effects but also limits the antitumor potency of this drug, which is dose-dependent [3]. Delivery of liposomal DOX has shown promise [3, 13], but the mechanism of drug release from these vehicles is unclear, complicating spatial and temporal control over delivery [14]. Polymeric nanoparticles have been employed as DOX-encapsulating vehicles; however, optimizing drug loading and tissue targeting for local delivery has proven difficult [14]. More general pharmacological strategies, such as administration of iron chelators, angiotensin-converting enzyme (ACE) inhibitors, or β-adrenergic blockers have been applied with varying degrees of success, but none have been validated in randomized clinical trials [1].

Other compounds that have been associated with cardiotoxicity include alcohol and cocaine. The invention intends to treat cardiotoxicity associated with these compounds even if such compounds are not used for therapeutic purposes.

Administration Timing, Routes and Formulations

The ligand dimers may be administered prior to, substantially simultaneously with, and/or after administration of the therapeutic agent associated with cardiotoxicity. For example, the ligand dimer may be administered prior to, or prior to and substantially simultaneously with, or prior to and after, or prior to, simultaneously with and after, or simultaneously with, or simultaneously with and after the therapeutic agent. In some important embodiments, it is administered substantially simultaneously with and/or after the therapeutic agent. As used herein, substantially simultaneously with means that two agents or compositions are administered to a subject within minutes of each other, or within the time it would take a medical practitioner to administer a first agent and then administer a second agent. The agents may be formulated together prior to administration or they may be formulated separately and administered separately to a subject.

The ligand dimers may be administered systemically by any one of a number of routes as described in greater detail below. Alternatively, in some important embodiments, the ligand dimers are administered locally to the heart. Local administration to or in the vicinity of the heart may be achieved by injection or infusion of a composition comprising the ligand dimer through a catheter. An example of such as delivery system is described in published US Patent Application 20020013615.

The ligand dimers can be used in soluble form or they can be tethered to a substrate, such as self-assembling peptides, a matrix (such as a biomaterial matrix), a tissue scaffold, or a bead. These ligand dimers may be attached to the substrates using a linker. The ligand dimers may be encapsulated in lipid-based microparticles or nanoparticles such as liposomes or solid lipid particles, or in polymer-based microparticles or nanoparticles such as PLGA particles. The soluble, tethered (or conjugated), or encapsulated forms of the ligand dimers may be administered systemically or they may be administered locally to the heart. Thus, in some embodiments, the ligand dimers are administered in sustained delivery formulations. Examples of such formulations are provided herein.

In some embodiments, the ligand dimer is administered in an amount, or by a route of administration that prevents the ligand dimer from having any appreciable direct effect on the condition calling for the anthracycline therapy. That is, in some embodiments, in the absence of the anthracycline therapy, the ligand dimer would have no effect on the underlying condition.

Other Cardioprotective Agents

The invention contemplates the use of other cardioprotective agents along with the ligand dimers of the invention. A cardioprotective agent is an agent that limits, prevents, or reduces the risk of therapy-induced cardiac damage (i.e., it protects cardiac tissue from damage resulting from a therapy). An example of an agent that reduces the risk of cardiotoxicity associated with anthracyclines is dexrazoxane (also known as Zinecard or Cardioxane).

Assessing Cardiotoxicity

With respect to the aspects of the invention relating to reducing the cardiotoxic effects of a therapeutic agent, the methods are directed to preventing, limiting or reversing the cardiotoxic effects induced by the therapeutic agent. These effects may be early (or acute) cardiotoxic effects or they may be late (or delayed) cardiotoxic effects.

Early cardiotoxicity may manifest itself as sinus tachycardia and/or electrocardiogram (ECG) abnormalities such as non-specific ST-T wave changes. Other less common manifestations include tachyarrhythmias such as premature ventricular contractions and ventricular tachycardia, bradycardia, and atrioventricular and bundle-branch block.

Late cardiotoxicity may manifest itself near the end of the course of treatment, or within 2-3 months following the cessation of treatment, or several months to years after the cessation of treatment. Late cardiotoxicity may manifest itself as a reduction in the left ventricular ejection fraction (LVEF), tachycardia, dyspnea, pulmonary edema, dependent edema, cardiomegaly, hepatomegaly, oliguria, ascites, pleural effusion, and gallop rhythm. Other less common manifestations include pericarditis and myocarditis. Those of ordinary skill in appreciate that many of the foregoing symptoms are indicative of heart failure, including congestive heart failure.

Ultimately whether the cardiotoxicity is early or late, it will negatively impact cardiac function. Cardiac function may be monitored in a number of ways, including without limitation multi-gated radionuclide angiography (MUGA), echocardiography (ECHO), or an ECG. These tests can be used to measure LVEF. Changes in an ECG profile may indicate dysrhythmias, a reduction of the QRS voltage, or a longer-than-normal systolic time interval, all of which may be indicative of cardiac dysfunction. Cardiac dysfunction may also be monitored by biomarker analysis, physical stress tests, imaging tests, etc. In rare instances, an endomyocardial biopsy can also be performed.

In some instances the ligand dimer prevents cardiotoxicity altogether, while in others it reduces the cardiotoxic effect as compared to a subject (or a population) that received the cardiotoxic therapeutic agent but not the ligand dimer. The effect of the ligand dimer in some embodiments of the invention may be determined by evaluating the subject prior to and after exposure to the therapeutic agent, determining the difference between those time points and then comparing such difference to subject (or a population of subjects) that was administered the therapeutic agent without the ligand dimer. The effect of the ligand in other embodiments may be determined by evaluating the subject after exposure to the therapeutic agent, determining the degree of cardiotoxicity, and comparing with a subject (or a population of subjects) that was administered the therapeutic agent without the ligand dimer. Data or information relating to a subject or a population of subjects that was administered by therapeutic agent but not the ligand dimer may be obtained in real-time or it may be historical data from prior analyses of the therapeutic agent, including for example pre-clinical, clinical and post-clinical data.

In still other instances, the ligand dimers may be used to reverse the cardiotoxic effects of certain therapeutic agents. This may entail administering a ligand dimer, such as an NRG dimer, to a subject after the therapeutic agent has been administered and, in some instances, after the cardiotoxic effects of the therapeutic agent have been identified. In these instances, the effect of the ligand dimer may be determined by comparing the degree of cardiotoxicity before and after administration of the ligand dimer. In these embodiments of the invention, the ligand dimer may be administered weeks, months, or even years after the last administration of the therapeutic agent.

In some instances, such cardiotoxicity leads to chronic conditions such as heart failure. Heart failure, in turn, may not manifest itself until several years after treatment. Accordingly, the invention intends to reduce the incidence, delay the onset, and/or reduce the severity and degree of early (or acute) cardiotoxicity, and/or reduce the incidence, delay the onset, or reduce the severity of late (or delayed) cardiotoxicity. In many instances, late (or delayed) cardiotoxicity is itself manifest as heart failure. Heart failure is discussed in greater detail herein.

Increasing Efficacy of Therapeutic Agents

In some aspects, the invention intends to increase the efficacy of a therapeutic agent that is associated with cardiotoxicity. The efficacy may be increased in a number of ways including increasing the dose administered to a subject, increasing the total amount administered to a subject, administering the agent more frequently, and/or administering the agent over a longer time course. Any one of these parameters, or any combination of these parameters, may be used in order to increase efficacy.

The normal tolerable dose of a therapeutic agent is typically determined during clinical testing and is known to medical practitioners. Such doses can also be determined by reference to a drug "label" issued by the FDA. In some instances, the tolerable dose may be a range and it will be routine practice for a medical practitioner to determine the most appropriate dose for a subject.

The invention therefore contemplates that the use of ligand dimers, such as NRG dimers, can allow doses of therapeutic agents higher than the normally tolerated doses to be administered. The increase in the dose (and alternatively or additionally the total amount of agent administered to the subject) may be about 5%, 10%, 15%, 20%, or 25% more than the dose that would have been tolerated in the absence of ligand dimers. In some instances, the medical practitioner may increase the dose until the level of cardiotoxic side effects approaches or becomes the level seen in the absence of the ligand dimer. The extent of the increase may depend on the individual subject, in some instances.

As an example, if the therapeutic agent is doxorubicin, the FDA label indicates that it is dosed at 60-75 mg/m$^2$ when used as a single agent, and at 40-60 mg/m$^2$ when used in combination within other cancer chemotherapeutic agents. The invention, in some instances, allows this dose to be increased about 5%, 10%, 15%, 20%, 25% or more The FDA label for doxorubicin also indicates that the risk of developing impaired myocardial function increases at cumulative doses of about 300 mg/m$^2$ and continues to rise in a dose dependent manner. The invention, in some instances, allows the cumulative dose to be increased about 5%, 10%, 15%, 15%, 20%, 25%, or more without a concomitant increase in the risk of developing impaired myocardial function.

The FDA label for doxorubicin also indicates that the drug is to be administered once every 21-28 days. The invention, in some instances, allows the drug to be delivered more frequently, including for example once every 20 days, once every 19 days, once every 18 days. once every 17 days, once every 16 days, once every 15 days, once every 14 days, or even more frequently.

Subjects

A subject can be any human or non-human vertebrate, e.g., mouse, rat, dog, cat, horse, cow, pig. Some methods of the invention are intended for subjects that will be administered, and/or that are being administered, and/or that have been administered therapeutic agents associated with cardiotoxicity. If the therapeutic agents are the anthracyclines, and more specifically doxorubicin, then these subjects may have disseminated neoplastic disorders such as acute lymphoblastic leukemia (ALL), acute myeloblastic leukemia (AML), Wilms' tumor, neuroblastoma, soft tissue and bone sarcomas, breast carcinoma, ovarian carcinoma, transitional cell bladder carcinoma, thyroid carcinoma, gastric carcinoma, Hodgkin's disease, malignant lymphoma, and bronchogenic carcinoma.

In some aspects of the invention, the subject may or may not have coronary artery disease and/or atherogenesis of the coronary arteries.

Myocardial Infarction

The invention further relates to another expected finding that bivalent NRG can provide benefit during and/or after myocardial infarction. Although not intending to be bound by any specific mechanism, this benefit may derive from the ability of bivalent NRG to enhance cardiac tissue regeneration by biasing receptor dimerization.

The ligand dimers of the invention may be administered at the onset of a myocardial infarction and/or after a myocardial infarction. Typically, they will not be administered prior to a myocardial infarction due to the unpredictability of the occurrence. The ligand dimers may be administered within days, within weeks, or within months of a myocardial infarction. Their effects may be determined by measuring infarct size, or one or more of the readouts listed herein for early or late cardiotoxicity.

Those of ordinary skill in the art, including but not limited to medical practitioners and medical emergency personnel, will be familiar with the characteristics of an MI. Symptoms of MI, particularly in men, include sudden chest pain (often times radiating to the left arm or left side of neck), shortness of breath, nausea, vomiting, palpitations, sweating, and anxiety. Symptoms in women differ somewhat from those in men, and typically include shortness of breath, weakness, indigestion, and fatigue. Whether in the presence or absence of such symptoms, MI may be detected using, for example, electrocardiograms, blood marker tests (e.g., creatine-kinase, troponin T or I), and heart imaging such as chest X-rays. Guidelines for diagnosing an MI include the WHO criteria (i.e., history of ischemic type chest pain lasting for more than 20 minutes, changes in serial ECG tracings, and rise/fall of serum cardiac markers such as creatine kinase MB and troponin) in which the presence of two and three such criteria indicate probable and definite MI, respectively.

Heart Failure

The invention further relates to another expected finding that bivalent NRG can provide benefit in chronic heart failure. Although not intending to be bound by any specific mechanism, bivalent NRG may enhance cardiac tissue regeneration by biasing receptor dimerization, thereby benefiting subjects having heart failure or dysfunction.

Heart failure is defined as the inability of the heart to pump blood through the body or to prevent blood from backing up into the lungs. Heart failure is often times referred to as congestive heart failure. It typically develops over time and may be triggered or exacerbated by another condition that causes heart tissue damage or that causes the heart tissue to work more (or harder) than normal. Examples of such conditions include without limitation an MI, exposure to cardiotoxicity-associated drugs such as anthracyclines, myocarditis, thyroid disease, viral infection, gingivitis, drug abuse, alcohol abuse, periocarditis, hypertrophic cardiomyopathy, left ventricular systolic dysfunction, and the like).

The invention provides, in some instances, methods for reducing the risk of heart failure in subjects, including in subjects who have undergone anthracycline therapy. The method is intended to reduce the risk of development and/or severity of heart failure. Development and severity of heart failure can be measured by monitoring and measuring symptoms or other characteristics associated with heart failure. These are discussed below. The methods may lead to the prevention of all or some such symptoms, the delayed onset of all or some such symptoms, and/or the reduction in the severity of all or some such symptoms. A reduction in the risk of heart failure may be determined by monitoring the symptoms or other characteristics associated with heart failure in the treated subject and comparing the number, onset, and severity of such symptoms or characteristics in that subject with historical population data for heart failure. For example, it is known that subjects that survive MI are more likely to develop heart failure than the average population. The methods of the invention aim to reduce this likelihood or risk of heart failure development.

Symptoms of heart failure include shortness of breath (dyspnea), swelling in the feet and legs (edema) typically as a result of abnormal fluid retention, fluid in the lungs, persistent coughing or wheezing, low exercise tolerance, general fatigue even in the absence of exercise, increased heart rate (or palpitations), loss of appetite, memory loss (or confusion), and nausea. One and typically more than one of these symptoms will be manifest in subjects having heart failure. The methods of the invention aim to prevent the development, delay the onset, and/or reduce the severity of one or more of these symptoms.

Heart failure can be diagnosed based on presentation of one and typically more than one of the foregoing symptoms. Heart failure can also be diagnosed or a suspected diagnosis of heart failure can be confirmed with tests such as an electrocardiogram (ECG or EKG), an echocardiogram ("cardiac echo"), or cardiac catheterization. Echocardiograms, for example, are able to measure the volume or fraction of blood that is ejected from the left ventricle with each beat. This is referred to as the ejection fraction. In normal subjects, about 60% of the blood in the left ventricle is ejected. Subjects may present with mildly depressed ejection fractions (e.g., 40-45%), moderately depressed ejection fractions (e.g., 30-40%), or severely depressed ejection fractions (e.g., 10-25%). Thus, in some aspects of the invention, the methods aim to maintain the ejection fraction, particularly if the subject presents with normal or mildly depressed ejection fractions. In some aspects, the methods of the invention aim to delay the onset of a depressed ejection fraction, regardless of the initial ejection fraction presentation. Stress tests may also be used to diagnose heart failure, and they may be combined with one or more of the imaging tests discussed above. For example, a stress test may be combined with an echocardiogram in order to monitor and measure heart function before, during and/or following exercise periods. Those of ordinary skill in the art, including medical practitioners and more particularly cardiologists, will be familiar these tests and their use in diagnosing heart function.

As used herein, the term "treat" means to have a positive or therapeutically beneficial effect on the likelihood, onset time, and/or severity of heart failure the subject may experience. Such positive or therapeutically beneficial effects may be measured by comparing the subject to a population that has not been subjected to the methods of the invention. The subject and the population can be compared in terms of incidence of heart failure, time of onset of heart failure, and severity of heart failure.

Ligand Monomers and Dimers

As discussed herein, the invention contemplates the use of neuregulin monomers and dimers in various aspects of the invention. The invention also provides and contemplates the use of other ErbB/HER ligand dimers. These include an EGF ligand dimer (EGF-EGF), a spitz ligand dimer (spitz-spitz), an EGF-NRG ligand dimer (EGF-NRG), an EGF-spitz ligand dimer (EGF-S), and a spitz-NRG ligand dimer (NRG-S). In still other embodiments, the invention contemplates the use of neuregulin-3 (NEU3) ligand dimers, neuregulin-4 (NEU4) ligand dimers, NEU3-EGF heterodimers, NEU3-spitz heterodimers, NEU4-EGF heterodimers, and NEU4-spitz heterodimers. It is to be understood that the notation used herein to refer to such ligand dimers is non-directional and is only intended to show the constituents of the dimer.

As will be understood, an EGF ligand homodimer induces HER1 homodimerization, a spitz ligand homodimer induces HER2 homodimerization, an EGF-NRG ligand heterodimer induces HER1-HER4 and/or HER1-HER3 heterodimerization, an EGF-spitz ligand heterodimer induces HER1-HER2 heterodimerization, and a spitz-NRG ligand heterodimer induces HER2-HER4 and/or HER2-HER3 heterodimerization.

The art is familiar with other ErbB/HER ligands, and these include HER1 ligands such as epidermal growth factor (EGF), transforming growth factor-alpha (TGF-α), epiregulin, heparin-binding epidermal-like growth factor (HB-EGF) and amphiregulin; HER3 ligands such as neuregulin-1α, heregulin-4 and β-cellulin; and HER4 ligands such as epiregulin, heparin-binding epidermal-like growth factor (HB-EGF), neuregulin-1α, neuregulin-3 and neuregulin-4. HER2 has no known ligand but it is activated upon heterodimerization with ligand-bound HER1, HER3 or HER4. HER2, among all receptors in the family, reportedly has the broadest range of interactions with intracellular signaling molecules. Accordingly, the invention provides and contemplates the use of the following ligand homo- and heterodimers in the compositions and methods provided herein: NRG2b-NRG2b, NRG2b-NRG2a, NRG2b-NRG1B3, NRG2b-NRG1a, NRG2b-EGF, NRG2b-NRG1B, NRG2b-NRG2, NRG2b-NRG3, NRG2b-NRG4, NRG2b-Epigen, NRG2b-amphiregulin, NRG2b-betacellulin, NRG2b-HB-EGF, NRG2b-TGF-alpha, NRG2b-Gurken, NRG2b-Keren, NRG2b-Spitz, NRG2b-Vein, NRG2a-NRG2a, NRG2a-NRG1B3, NRG2a-NRG1a , NRG2a-EGF, NRG2a-NRG1B, NRG2a-NRG2, NRG2a-NRG3, NRG2a-NRG4, NRG2a-Epigen, NRG2a-amphiregulin, NRG2a-betacellulin, NRG2a-HB-EGF, NRG2a-TGF-alpha, NRG2a-Gurken, NRG2a-Keren, NRG2a-Spitz, NRG2a-Vein, NRG1B3-NRG1B3, NRG1B3-NRG1a , NRG1B3-EGF, NRG1B3-NRG1B, NRG1B3-NRG2, NRG1B3-NRG3, NRG1B3-NRG4, NRG1B3-Epigen, NRG1B3-amphiregulin, NRG1B3-betacellulin, NRG1B3-HB-EGF, NRG1B3-TGF-alpha, NRG1B3-Gurken, NRG1B3-Keren, NRG1B3-Spitz, NRG1B3-Vein, NRG1a-NRG1α, NRG1a-EGF, NRG1a-NRG1B, NRG1a-NRG2, NRG1a-NRG3, NRG1a-NRG4, NRG1a-Epigen, NRG1a-amphiregulin, NRG1a-betacellulin, NRG1a-HB-EGF, NRG1a-TGF-alpha, NRG1a-Gurken, NRG1a-Keren, NRG1a-Spitz, NRG1a-Vein, EGF-EGF, EGF-NRG1B, EGF-NRG2, EGF-NRG3, EGF-NRG4, EGF-Epigen, EGF-Epiregulin, EGF-amphiregulin, EGF-betacellulin, EGF-HB-EGF, EGF-TGF-alpha, EGF-Gurken, EGF-Keren, EGF-Spitz, EGF-Vein, NRG1B-NRG1B, NRG1B-NRG2, NRG1B-NRG3, NRG1B-NRG4, NRG1B-Epigen, NRG1B-amphiregulin, NRG1B-betaceullin, NRG1B-HB-EGF, NRG1B-TGF-alpha, NRG1B-Gurken, NRG1B-Keren, NRG1B-Spitz, NRG1B-Vein, NRG2-NRG2, NRG2-NRG3, NRG2-NRG4, NRG2-Epigen, NRG2-epiregulin, NRG2-amphiregulin, NRG2-betacellulin, NRG2-HB-EGF, NRG2-TGF-alpha, NRG2-Gurken, NRG2-Keren, NRG2-Spitz, NRG2-Vein, NRG3-NRG3, NRG3-NRG4, NRG3-epigen, NRG3-epiregulin, NRG3-amphiregulin, NRG3-betacellulin, NRG3-HB-EGF, NRG3-TGF-alpha, NRG3-Gurken, NRG3-Keren, NRG3-Spitz, NRG3-vein, NRG4-NRG4, NRG4-Epigen, NRG4-epiregulin, NRG4-amphiregulin, NRG4-betacellulin, NRG4-HB-EGF, NRG4-TGF-alpha, NRG4-Gurken, NRG4-Keren, NRG4-Spitz, NRG4-Vein, Epigen-epigen, epigen-epiregulin, epigen-amphiregulin, epigen-betacellulin, epigen-HB-EGF, epigen-TGF-alpha, epigen-Gurken, epigen-Keren, epigen-Spitz, epigen-vein, epiregulin-epiregulin, epiregulin-amphiregulin, epiregulin-betacellulin, epiregulin-HB-EGF, epiregulin-TGF-alpha, epiregulin-gurken, epiregulin-keren, epiregulin-spitz, epiregulin-vein, amphiregulin-amphiregulin, amphiregulin-betacellulin, amphiregulin-HB-EGF, amphiregulin-TGF-alpha, amphiregulin-gurken, amphiregulin-keren, amphiregulin-spitz, amphiregulin-vein, betacellulin-betacellulin, betacellulin-HB-EGF, betacellulin-TGF-alpha, betacellulin-gurken, betacellulin-keren, betacellulin-spitz, betacellulin-vein, HB-EGF-HB-EGF, HB-EGF-TGF-alpha, HB-EGF-gurken, HB-EGF-keren, HB-EGF-spitz, HB-EGF-vein, TGF-alpha-TGF-alpha, TGF-alpha-gurken, TGF-alpha-keren, TGF-alpha-spitz, TGF-alpha-vein, gurken-gurken, gurken-keren, gurken-spitz, gurken-vein, keren-keren, keren-spitz, keren-vein, spitz-spitz, spitz-vein, and vein-vein.

In some embodiments, one or both of the ligands of the ligand dimers is not an antibody or an antigen-binding antibody fragment.

Receptor dimer features can guide the design of ligand dimers (spacing, orientation, binding residues, termini accessibility, etc.). In the ligand dimers provided, the two ligands are linked with a linker such that the ligand dimer can force the dimerization of a specific receptor pair. The linker, for example, can comprise a coiled coil. A coiled coil is a structural motif in proteins, in which, in general, two to seven alpha-helices are coiled together like the strands of a rope. In some embodiments, the coiled coil of the ligand dimer is one with two alpha-helices coiled together. Such a ligand dimer can be formed by first attaching a ligand to one single alpha helix coiled coil domain (i.e., one ligand monomer) separately from another ligand attached to a single alpha helix coiled coil domain (i.e., another ligand monomer) and contacting the two ligand monomers such that the ligand dimer is formed through an interaction with the two alpha helix coiled coil domains, for example, at concentrations of approximately 1 nM. In some embodiments the coils comprise a peptide comprising or consisting of the amino acid sequence of LEI EAAFLEQ ENTALET EVAELEQ EVQRLEN IVSQYET RYGPLGGGK (SEQ ID NO:1) or KGGGLEI RAAFLRR RNTALRT RVAELRQ RVQRLRN IVSQYET RYGPL (SEQ ID NO:2). In some embodiments the interaction of the coils of a coiled coil exhibits a Kd of no more than $1\times10^{-10}$, $1\times10^{-11}$, $1\times10^{-12}$, $1\times10^{-13}$, $1\times10^{-14}$ or $1\times10^{-15}$ M. The linker can also comprise a peptide spacer. For example, the peptide spacer can be on either or both ends of the coiled coil. Each of the peptide spacers can be attached to a single alpha helix coiled coil domain of the coiled coil. The peptide spacer can be, for example, a peptide of 5, 6, 7, 8, 9, 10, 15, 20, 25, 30, 35, 40, 45 or 50 amino acids or more. The number of amino acids in the peptide spacer may be, in some embodiments, 20 amino acids or up to 10 amino acids greater or fewer, depending on the particular ligand and length of coil. The ligand spacing can influence avidity through its control of binding/dissociation kinetics and can be used to tune avidity.

The linker can also comprise a water soluble flexible polymer with or without spacers on either or both ends. Examples of spacers are as provided immediately above. The water soluble flexible polymer is one that can covalently link the two ligands together, is biocompatible, does not interfere with the desired signaling effects and allows for the forced dimerization of a specific receptor pair. Water soluble flexible polymers include polyethylene oxide (PEO), dextran, polyacrylic acid and polyacrylamide.

The length of the linker required can be determined with methods known to those of ordinary skill in the art. In general, the length of the linker is dependent on the distance between receptor ligand sites. For example, the length of the linker can be determined based on a calculus using the radius of gyration. Generally, for the linkers specifically provided herein the radius of gyration is calculated according to the following:

Radius of gyration=$c*n^{3/5}$, where $c$ is a constant that depends on the type of polymer For example, when PEO is the polymer, c is 0.3 nM. In some embodiments, the length of the linker is within 50% of the radius of gyration. As an example, the length of the linker may be equal to the radius of gyration. The length of the linker, in some embodiments, is in the range of 20 nm to 10,000 nm. In other embodiments, the length of the linker is in the range of 80 nm to 10,000 nm. In still other embodiments, the length of the linker is in the range of 100 nm to 10,000 nm. In still other embodiments, the length of the linker is in the range of 20 nm to 1,000 nm. In other embodiments, the length of the linker is in the range of 80 nm to 1,000 nm. In still other embodiments, the length of the linker is in the range of 100 nm to 1,000 nm. In a further embodiment, the length of the linker is about 200 nm.

The ligand dimers provided can be produced with the methods provided herein or that are otherwise known in the art. As an example, various methods for producing ligand dimers are described in PCT application PCT/US2009/005252, entitled "Compositions of and Methods of Using Ligand Dimers," and these methods are incorporated by reference herein. The binding of ligand dimers to receptors can be assessed by binding assays which include, for example, far Western spot blot, immunofluorescence binding assay (ELISA-based), surface plasmon resonance (SPR-Biacore), isothermal titration calorimetry (ITC), cross-linking and SDS-PAGE, high resolution size exclusion chromatography (HRSEC) and native gels.

Bioactivity of the receptors can be assessed with probes. Such probes include antibodies, such as antibodies to a pan HER downstream marker (e.g., pERK (T202/Y204)) as well as antibodies that are receptor specific (e.g., pHer-1(Y1068), pHer-2(Y1221), pHer-3(Y1289) and pHer-4(Y1284)). Inhibitors of Her bioactivity can also be used in assays to assess bioactivity. Such inhibitors include small molecules (e.g., Her-1/AG1478, pan Her "CFAB") and RNAi. For example, validated siRNAs are available for all HER receptors. Alternatively, RNAi are available in lentiviral packaging vectors to facilitate transduction of recalcitrant cell types, such as MSCs. Bioactivity can also be assessed with dose response assays (e.g., that measure pERK activation, such as at 10 minutes) and time course assays (e.g., that measure pERK activation over time). The conditions under which such assays can be conducted include, for example, under serum starvation at about 12 hours with 0.1% FBS medium and a ligand concentration of 10 pM-100 nM. The assays can be, for example, in cell Western or a Western blot and can also include the use of a LI-COR ODYSSEY IR dye scanner.

Binding and internalization of ligands can be measured with, for example, radio-labeling experiments that can quantitatively measure binding affinity and internalization of ligand/receptor complexes. The differences in binding affinity would be expected to be due to the bivalent interaction with receptor dimers (avidity effect). Differences in receptor trafficking between native and bivalent ligands would also suggest biased receptor pairings (e.g., Her-1 homodimers are trafficked at higher rates than other dimers).

Bivalent ligand induced receptor dimerization bias can be confirmed with biochemical assays and phenotypic assays. Biochemical assays include Her receptor FRET fusions (e.g., Her-1-CFP, Her-3-YFP), Her-receptor complementation fusion (e.g., luciferase or DHFR); receptor crosslinking (e.g., blot for all Her receptors), coimmunoprecipitation (e.g., pull down Her-1, blot for Her-x) and mass spectrometry of Y/pY. Phenotypic assays include assays for proliferation, cell death migration and differentiation.

A phenotypic assay can be performed to assess proliferation and/or cell death. As an example, proliferation of HeLa, MCF-7 and hTMSCs under various ligand conditions can be measured at 48 and 96 hours using a CYQUANT assay. The experiment can be performed with low serum (1%). The ligands are all at a concentration of 50 nM as one example. Bivalent ligand forms may signal less potently than monovalent or native forms and may lead to less proliferation due to exclusion of Her-2 signaling complexes.

Another phenotypic assay can be one that assesses migration. Migration on 2D surfaces using any type of biotinylated substrate (e.g., PMMA/PEG-biotin gels, commercial biotin-substituted 96-well plates, etc.) can be used to assess the effects of tethered ligands on migration of MSCs. Time lapse microscopy can be used to measure speed and persistence of MSCs under various ligand conditions. Characterization of surface biotinylation can also be performed with functionalization with biotinylated C1(EGF).

Pharmaceutical Compositions, Formulations, Effective Amounts, Administration Routes Effective amounts of the ligand dimers provided are administered to a subject in need of such treatment. Effective amounts are those amounts which will result in a desired improvement in the condition or symptoms of the condition, e.g., for cancer this is a reduction in cellular proliferation or metastasis, without causing other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In general, when administered for therapeutic purposes, the formulations provided are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions provided may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the subject matter provided herein. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); and parabens (0.01-0.25% W/V).

Provided herein are pharmaceutical compositions, for medical use, which comprise a ligand dimer together with one or more pharmaceutically acceptable carriers and optionally other therapeutic ingredients. The term "pharmaceutically-acceptable carrier" as used herein, and described more fully below, means one or more compatible solid or liquid filler, diluants or encapsulating substances which are suitable for administration to a human or other animal. As used herein, the term "carrier" denotes an organic or inorganic ingredient, natural or synthetic, with which the active ingredient is combined to facilitate the application. The components of the pharmaceutical compositions also are capable of being commingled with a ligand dimer or other composition, and with each other, in a manner such that there is no interaction which would substantially impair the desired pharmaceutical efficiency.

Unless otherwise stated herein, a variety of administration routes are available. The particular mode selected will depend, of course, upon the particular active agent selected, the particular condition being treated and the dosage required for therapeutic efficacy. The methods provided, generally speaking, may be practiced using any mode of administration that is medically acceptable, meaning any mode that produces effective levels of a desired response without causing clinically unacceptable adverse effects. One mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, transdermal, etc. As stated herein, one preferred route of administration in some aspects of the invention is local administration in or near the heart.

For oral administration, the compounds can be formulated readily by combining the active compound(s) with pharmaceutically acceptable carriers well known in the art. Such carriers enable the compounds to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described elsewhere herein, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The compositions may conveniently be presented in unit dosage form and may be prepared by any of the methods well known in the art of pharmacy. All methods include the step of bringing the ligand dimers into association with a carrier which constitutes one or more accessory ingredients. In general, the compositions are prepared by uniformly and intimately bringing the ligand dimers into association with a liquid carrier, a finely divided solid carrier, or both, and then, if necessary, shaping the product. The compositions may be stored lyophilized.

Other delivery systems can include time-release, delayed release or sustained release delivery systems. Such systems can avoid repeated administrations of the ligand dimers provided, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Additional Therapies

The ligand dimers of the invention may be used in combination with other therapies or procedures aimed at reducing the risk or severity of early or late cardiotoxicity, and/or heart failure. These therapies include without limitation digitalis, diuretics, antiplatelet drug therapy including fibrinolytic agents, anti-coagulation agents, and platelet function inhibitors, beta blocker therapy, ACE inhibitor therapy, statin therapy, aldosterone antagonist therapy (e.g., eplerenone), and omega-3-fatty acids therapy. These and other suitable therapies are discussed in greater detail below.

Fibrinolytic agents are agents that lyse a thrombus (e.g., a blood clot), usually through the dissolution of fibrin by enzymatic action. Examples include but are not limited to ancrod, anistreplase, bisobrin lactate, brinolase, Hageman factor (i.e. factor XII) fragments, molsidomine, plasminogen activators such as streptokinase, tissue plasminogen activators (TPA) and urokinase, and plasmin and plasminogen.

Anti-coagulant agents are agents that inhibit the coagulation pathway by impacting negatively upon the production, deposition, cleavage and/or activation of factors essential in the formation of a blood clot. Anti-coagulant agents include but are not limited to vitamin K antagonists such as coumarin and coumarin derivatives (e.g., warfarin sodium); glycosoaminoglycans such as heparins both in unfractionated form and in low molecular weight form; ardeparin sodium, bivalirudin, bromindione, coumarin dalteparin sodium, desirudin, dicumarol, lyapolate sodium, nafamostat mesylate, phenprocoumon, sulfatide, tinzaparin sodium, inhibitors of factor Xa, factor TFPI, factor VIIa, factor IXc, factor Va, factor VIIIa as well as inhibitors of other coagulation factors.

Inhibitors of platelet function are agents that impair the ability of mature platelets to perform their normal physiological roles (i.e., their normal function). Examples include but are not limited to acadesine, anagrelide, anipamil, argatroban, aspirin, clopidogrel, cyclooxygenase inhibitors such as nonsteroidal anti-inflammatory drugs and the synthetic compound FR-122047, danaparoid sodium, dazoxiben hydrochloride, diadenosine 5',5'''-P1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin ($PGI_2$), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and anti-serotonin drugs, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine.

Anti-inflammatory agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. One preferred anti-inflammatory agent is aspirin.

Lipid reducing agents include gemfibrozil, cholystyramine, colestipol, nicotinic acid, probucol lovastatin, and statins such as fluvastatin, simvastatin, atorvastatin, pravastatin, and cirivastatin.

Direct thrombin inhibitors include hirudin, hirugen, hirulog, agatroban, PPACK, thrombin aptamers.

Glycoprotein IIb/IIIa receptor inhibitors are both antibodies and non-antibodies, and include but are not limited to ReoPro (abcixamab), lamifiban, tirofiban.

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

Beta-adrenergic receptor blocking agents (also known as beta blockers) are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol,7-(2-hydroxy-3-t-butylaminpropoxy)phthalide. The above-identified compounds can be used as isomeric mixtures, or in their respective levorotating or dextrorotating form.

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include but are not limited to peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

ACE inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451);

fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885, 292); monoclonal antibodies to renin (U.S. Pat. No. 4,780, 401); and a variety of other peptides and analogs thereof (U.S. Pat. Nos. 5,071,837, 5,064,965, 5,063,207, 5,036,054, 5,036, 053, 5,034,512, and 4,894,437).

HMG-CoA reductase inhibitors include, but are not limited to, statins such as simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985, 5,135,935, 5,356,896, 4,920,109, 5,286,895, 5,262,435, 5,260,332 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

It is to be understood that the invention contemplates the use of one or more of any of the foregoing agents in combination with ligand dimers of the invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Introduction

The development of improved cardioprotective and/or cardioregenerative therapies that do not inhibit the anti-cancer effects of doxorubicin (DOX) would increase cancer cure rates and improve the length and quality of life for cancer survivors. An agent that can be used for cardioprotection against DOX side effects is the epidermal growth factor (EGF) family member neuregulin-1β (NRG).

In the postnatal heart, NRG binds its cognate receptor ErbB4 with high affinity, leading predominantly to the formation of ErbB4/ErbB2 heterodimers, and, to a lesser degree, ErbB4/ErbB4 homodimers. These events may lead to distinct signaling outcomes that may be synergistic or antagonistic. Thus, biasing the formation of receptor dimers may allow for new therapeutic effects that are superior to those resulting from the natural distribution of receptor dimers formed by native monomeric NRG. For example, participation of ErbB2 in dimers formed following contact with native NRG may not be beneficial in reducing DOX-induced apoptosis [9], and therefore the therapeutic efficacy of native NRG may be diluted by its natural propensity to form ErbB2/ErbB4 heterodimers.

Bivalent NRG ligands capable of biasing ErbB receptor dimerization/oligomerization/aggregation have been successfully engineered, and the preliminary data indicate that these engineered proteins are more effective than their native counterparts against DOX-induced cardiotoxicity. NRG has shown efficacy against DOX-induced cardiotoxicity in vitro [9] and in vivo [4, 5]. The ligand dimers of the invention are demonstrated herein to be more effective than NRG monomers used in these previous studies.

In addition, constraining administration of NRG to the cardiac microenvironment may further improve its activity against DOX-induced cardiotoxicity [10-12]. The following examples describe the expression and purification of new fusion proteins to facilitate local delivery of native and/or engineered NRG to the myocardium. These experiments will employ a peptide nanofiber system to compare the effects of local and systemic NRG delivery in vivo.

Regimens combining DOX or other anthracyclines with antibodies against ErbB2 such as trastuzumab (Herceptin) have been used for patients with invasive breast cancer marked by an overexpression of ErbB2 [2]. Interestingly, in addition to DOX-induced cardiotoxicity, blocking ErbB2 also induces a cardiotoxic effect, thought to be the result of partial inhibition of intrinsic NRG signaling [2]. Nevertheless, ErbB2 is overexpressed in a number of cancers, and blockade of its activity is a growing area of therapeutic investigation in oncology [16]. Thus, the ability to induce cardioprotective effects with NRG by biasing towards ErbB4 homodimerization, and thereby reducing signaling via ErbB2, would be especially valuable in enabling antitumor therapies.

NRG was previously reported to be one of the few molecules capable of inducing cell-cycle reentry and division of differentiated cardiomyocytes in vitro and in vivo [6]. It was also previously shown that NRG promotes replacement of cardiomyocytes when administered up to 1 week following induced myocardial infarction, leading to decreased scar formation [6]. However, the overall level of cardiomyocyte division reported may not be clinically sufficient. Thus, it is important to determine if biasing ErbB receptor dimerization towards formation of ErbB4 homodimers can improve cardiac effects of NRG. By doing so, treatment of a cohort of patients currently suffering from DOX-induced cardiomyopathy may be possible, and application of the proposed therapy may not be limited to scheduled co-administration with DOX.

NRG binds with high affinity to ErbB4 ($K_d$~0.7 nM) while having no significant affinity for ErbB1 ($K_d$~5550 nM) [18]. Hence, NRG initiates signaling in cardiomyocytes predominantly via induction of ErbB4 homodimers and ErbB2/ErbB4 heterodimers (FIG. 2B), the latter of which assemble with higher frequency than the former [8]. As it relates to cardioprotection from DOX-induced cardiomyopathy, the impact of NRG-induced heterodimer versus homodimer formation on downstream signaling in cardiomyocytes is unclear. One report indicates that NRG stimulation of the pro-survival PI3k/Akt pathway is primarily driven by ErbB4 homodimers [17], while other studies demonstrate that NRG induces the same pathway in an ErbB2-dependant manner, implying that heterodimer formation is critical [6, 19]. Both homodimers and heterodimers are formed in the presence of NRG, and therefore the therapeutic effects of this protein are likely mediated by downstream signaling from both dimer pairs. However, it is possible that a shift towards either hetero- or homo-dimerization may enhance productive signaling outcomes and/or diminish counterproductive regimes.

Design of Engineered Ligands for Biasing ErbB Receptor Dimerization

Figure 2:
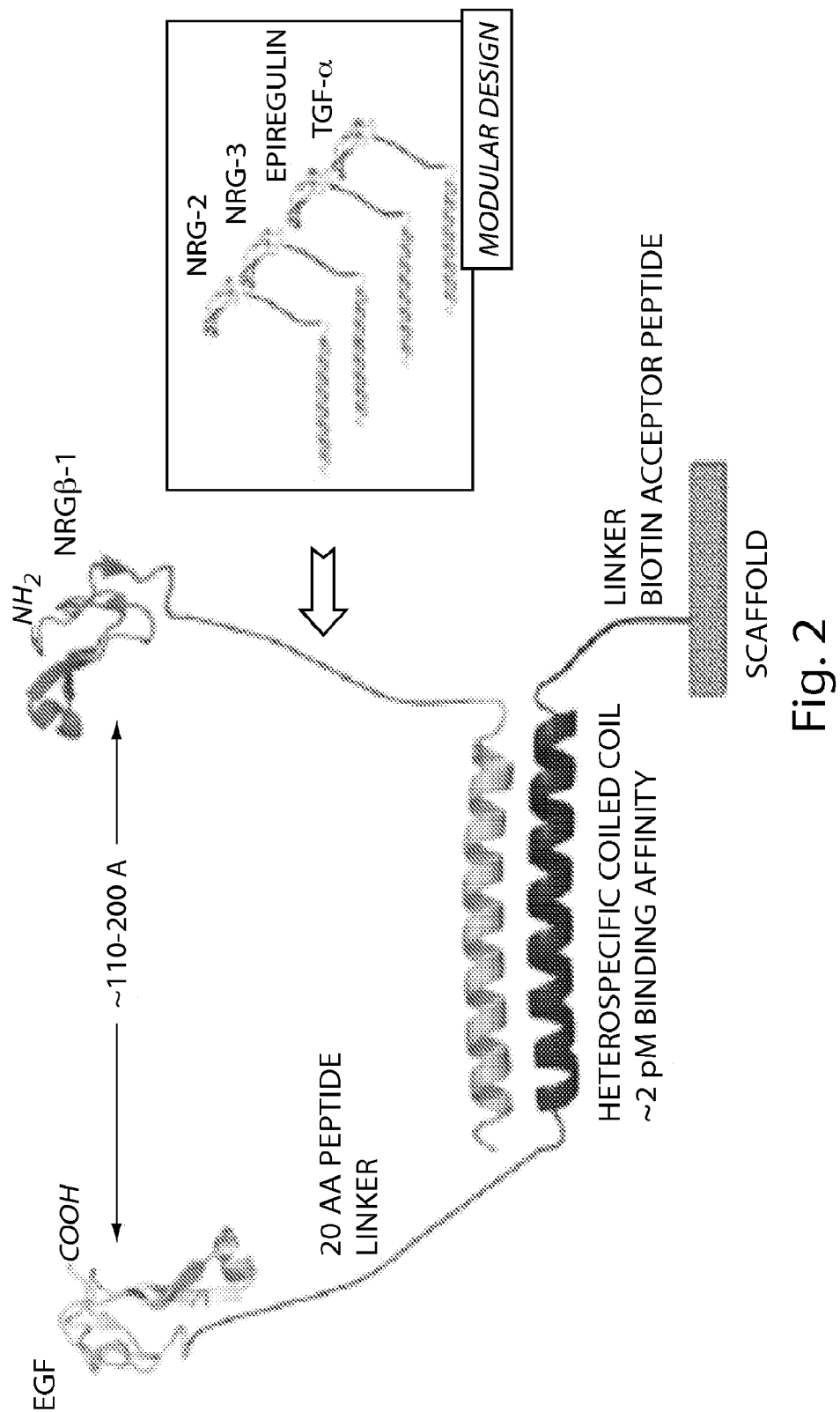
FIG. 2. Design of engineered ligands for biasing ErbB receptor dimerization. Schematic of the modular design of bivalent ligands. Complimentary high affinity coiled coil domains enable formation of spatially constrained bivalent ligands. In this example, heterospecific coiled constructs were designed to enable the formation of a NRG-EGF dimer ligand. The modular design allows confirmation of protein expression and refolding by bioactivity testing of each modular component.

To exert control over ErbB receptor dimerization, a modular approach was employed whereby two proteins were coupled via a highly specific ($K_d$=10-15 M) coiled binding region [20]. The resulting bivalent ligands should then be capable of recruiting specific receptors into dimer complexes, based on the affinities and specificities of EGF family ligands for particular ErbB receptors. The design of the engineered ligands was first guided by the crystal structures of dimerized ErbB receptors. X-ray diffraction of ligand-bound ErbB extracellular domains revealed that the distance between ligands in a dimerized receptor is approximately 10 nm [21]. In the bivalent construct, the proteins themselves are separated from the coil region by a previously designed protease resistant spacer [22] that confers flexibility, solubility, and, together with the coils, a sufficient extension to bridge a gap 20 nm long, reducing the possibility of steric hindrance of dimer formation. Additionally, a biotin acceptor peptide (BAP) sequence was incorporated into the engineered ligands to permit biotinylation and subsequent immobilization on neutravidin-coated peptide nanofibers or other biomaterial scaffolds. The modularity of the described system facilitates the investigation of numerous ligand combinations without requiring multiple cloning, expression, and purification strategies and optimization. An overview of the engineered ligand design is depicted in FIG. 2, showing a bivalent ligand of NRG and EGF.

Local Protein Delivery to the Myocardium and the Use of Self-Assembling Peptide Nanofibers Proteins are an important class of drugs due to their highly specific interactions with target receptors and their multifunctionality [23]. However, their short half-lives, low diffusivity into tissue, relatively large size, and potential induction of toxicity at high systemic doses can limit the efficacy of conventional routes of administration [24]. Local delivery of proteins enables targeting to a specific population of cells, reducing the possibility of deleterious effects on other tissues. In the myocardium, a number of vehicles for local delivery have been employed, including self-assembling peptide nanofibers. Self-assembling peptides are characterized by periodic repeats of alternating ionic hydrophilic and hydrophobic amino acids; the hydrophilic amino acids are alternately repeating units of positively charged (lysine or arginine) and negatively charged (aspartate and glutamate) residues. Such structures naturally form beta-sheets with distinctive polar and non-polar surfaces [25, 26]. Nanofiber scaffolds with a peptide content of 1-10 mg/ml (>99% water) are formed when the peptide solution is exposed to physiological medium or salt solution [27, 28] and consist of individual interwoven nanofibers approximately 10-20 nm in diameter. Using this approach, platelet-derived growth factor-BB (PDGF-BB) has been shown to be cardioprotective in ischemia/reperfusion injury [11] and stromal-derived factor-1 (SDF-1) to recruit stem cells after myocardial infarction [10].

Validation of Engineered ErbB Receptor Ligands

Figure 3A:
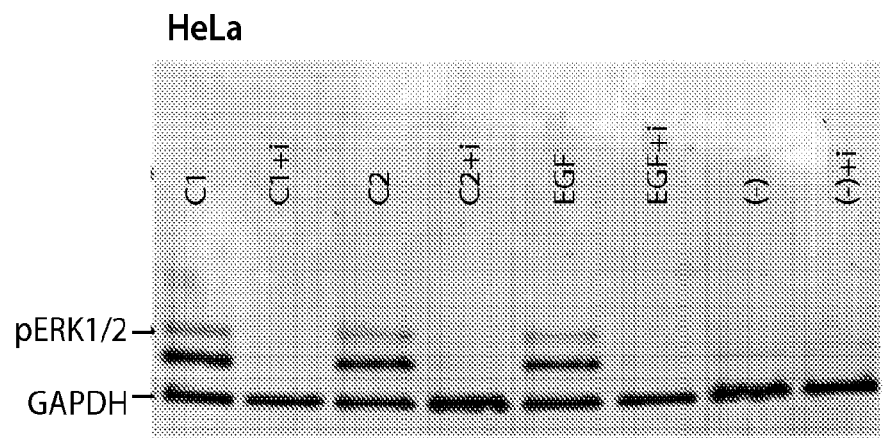
FIG. 3A (HeLa), FIG. 3B (MCF-7).
Figure 3B:
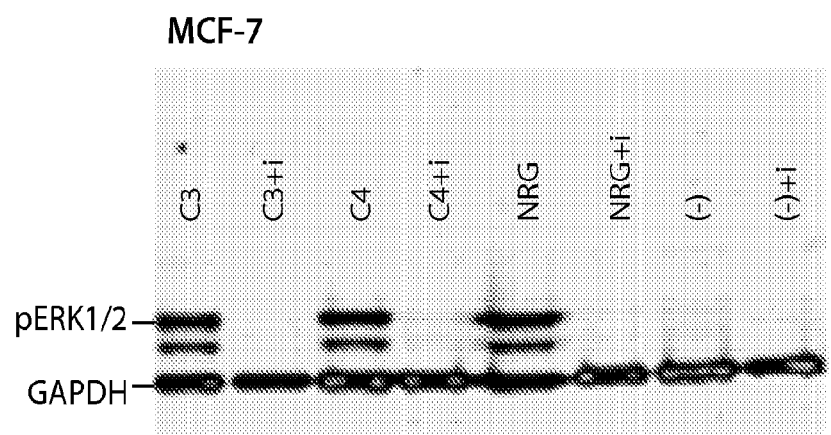
FIG. 3. Bioactivity of engineered ligands. Stimulation of ERK phosphorylation by engineered EGF (C1, C2) and NRG (C3, C4) compared to native protein. Inhibition of phosphorylation was accomplished via a pan-ErbB kinase inhibitor N-(4-((3-Chloro-4-fluorophenyl)amino)-pyrido[3,4-d]pyrimidin-6-yl)2-butynamide (i), indicating specificity.

Proteins are produced using a maltose binding protein (MBP) tagged system (pMAL-c2X, New England Biolabs). Proteins are analyzed by Coomassie staining, immunoblotting, mass spectrometry, absorbance at 280 nm, and in vitro cell response versus wild type ligands EGF and NRG. Specificity for ErbB receptor activation was further assessed by including inhibitor controls using the pan-ErbB kinase inhibitor N-(4-((3-Chloro-4-fluorophenyl)amino)-pyrido[3,4-d]pyrimidin-6-yl)-2-butynamide. Bioactivity and ErbB specificity were validated in HeLa and MCF-7 cells (for EGF and NRG containing ligands, respectively) (FIG. 3). HeLa cells express EGFR and ErbB2 and are responsive to EGF while MCF-7 cells express ErbB3 and ErbB4 and are responsive to NRG. Monovalent engineered ligands produced pERK activation indistinguishable from their native analogues, as predicted, and activation was specifically inhibited by a pan-ErbB kinase inhibitor.

Figure 4A:
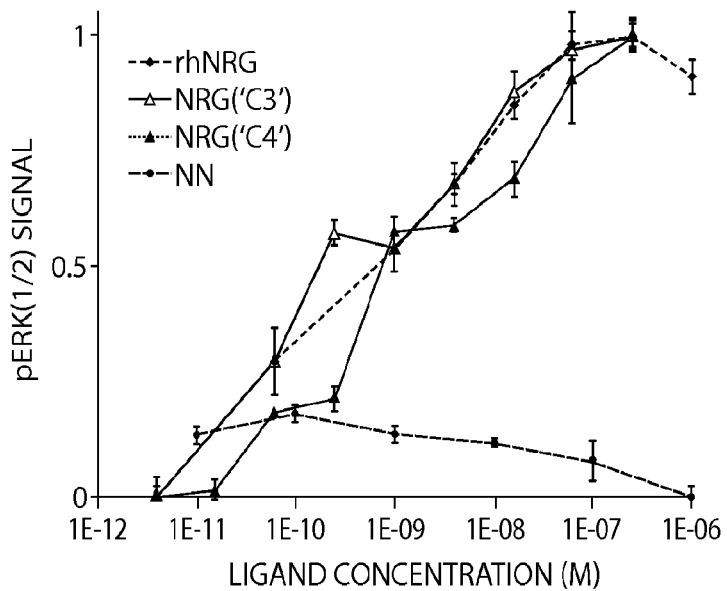
FIG. 4. Cellular responses differ between native and bivalent NRG. (A) hTMSC were exposed to native (rhNRG), monovalent (C3, C4) and bivalent (NN) NRG in culture. ERK phosphorylation was measured via western analysis and quantified by densitometry. (B) Stimulation with native and monovalent NRG resulted in a dose-dependent increase in ERK phosphorylation, while addition of bivalent NRG led to reduced pERK, indicative of increased formation of ErbB3 homodimers, which lack kinase domains.
Figure 4B:
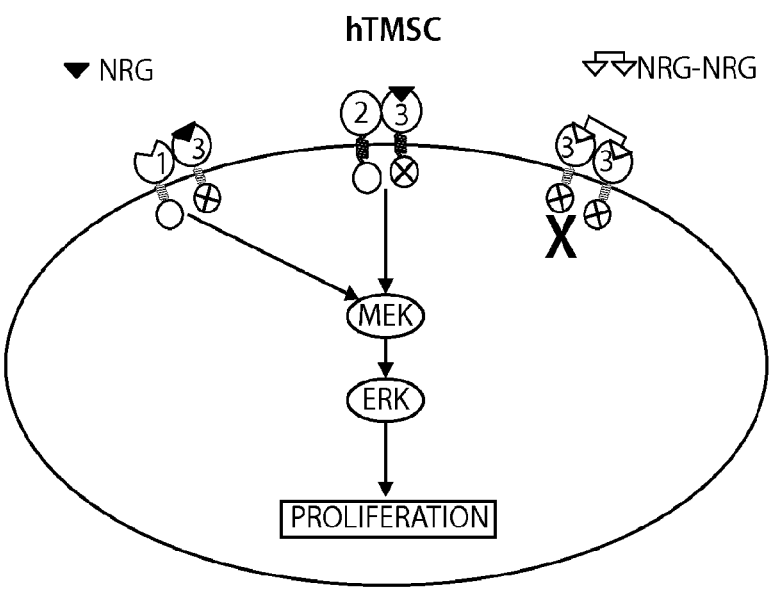

To demonstrate the ability of engineered ligands to bias ErbB receptor dimerization, bivalent NRG was administered to human telomerase reverse transcriptase (hTERT)-immortalized human mesenchymal stem cells (hTMSC), which are known to express ErbB1, ErbB2, and ErbB3, with no expression of ErbB4 [29]. Since NRG has high affinity for ErbB3 as well as ErbB4, and since ErbB3 is kinase-deficient, recruitment of ErbB3 homodimers via bivalent NRG should produce a null signaling outcome, whereas native or monovalent engineered NRG should be capable of stimulating ERK phosphorylation in these cells via ErbB2/ErbB3 mediated signaling. FIG. 4A shows a robust dose-dependent pERK response to both configurations of engineered monovalent NRG (C3, C4) similar to native NRG, as expected. In contrast, stimulation with bivalent NRG appears to activate ERK modestly at low concentrations, but this mild effect is erased at higher doses, consistent with the predicted ErbB3 homodimerization induced by bivalent NRG, which results in lack of signal propagation (FIG. 4B).

Efficacy of Engineered ErbB Receptor Ligands in the Cardiac System

Figure 5A:
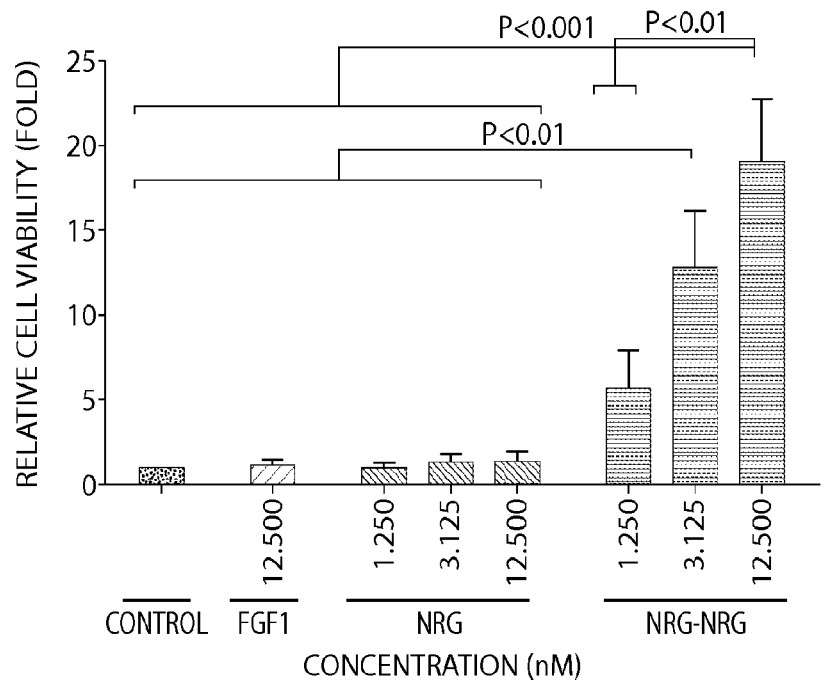
FIG. 5. Bivalent NRG attenuates doxorubicin-induced toxicity to cardiomyocytes in vitro. (A) Neonatal rat cardiomyocytes (NRCM) were simultaneously exposed to doxorubicin (1 µM) and either fibroblast growth factor-1 (FGF1, a known NRCM mitogen), native NRG (NRG), or bivalent NRG (NRG-NRG) at the indicated doses. Cell viability, as measured by the cell titer blue assay, was significantly increased in NRCM treated with bivalent NRG compared to native NRG, FGF1, and unstimulated cells (control). (B) Bivalent NRG may preferentially activate the PI3K/Akt pro-survival signaling pathway.
Figure 5B:
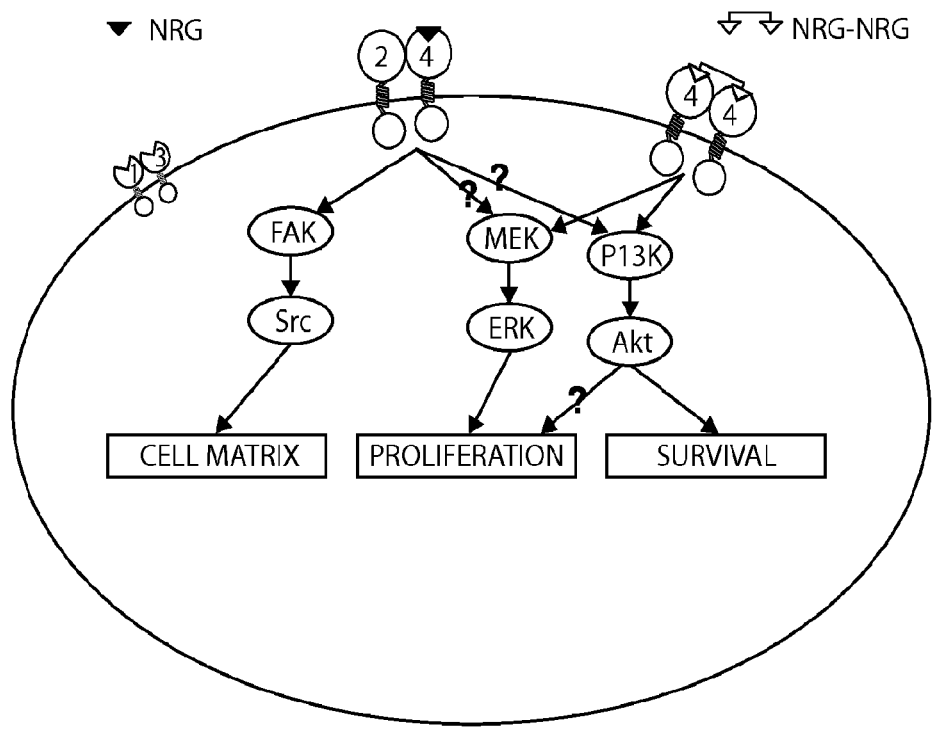

The activity of engineered ErbB receptor ligands has been verified in multiple cell systems. ErbB receptor profiles in cardiomyocytes are distinct. The efficacy of engineered bivalent ligands has been tested on cardiomyocytes in culture. Specifically, the effects of native and bivalent NRG on cardiomyocytes exposed to DOX-induced cytotoxicity were examined. A number of studies have demonstrated the efficacy of NRG against DOX-induced cardiotoxic effects [4, 5], with evidence indicating that ErbB2-mediated signaling is crucial to this outcome [15, 30]. Therefore, it was initially hypothesized that stimulation of DOX-exposed cardiomyocytes with bivalent NRG—which should preferentially induce ErbB4/ErbB4 homodimers—would be less effective at protecting against cytotoxic effects than native NRG, which preferentially induces ErbB2/ErbB4 heterodimers while also forming ErbB4 homodimers [8]. However, the results obtained from these experiments were surprising; bivalent NRG induced a dramatically more robust protective effect than did native NRG (FIG. 5A). A possible explanation for this result is the ability of ErbB4 homodimers to activate PI3 kinase (FIG. 5B), leading to induction of the canonical Akt-mediated survival pathway in cardiomyocytes [9, 17]. If this effect of bivalent NRG is validated in vivo, it could have significant potential as a new cardioprotective agent against DOX-induced cardiomyopathy.

Figure 6:
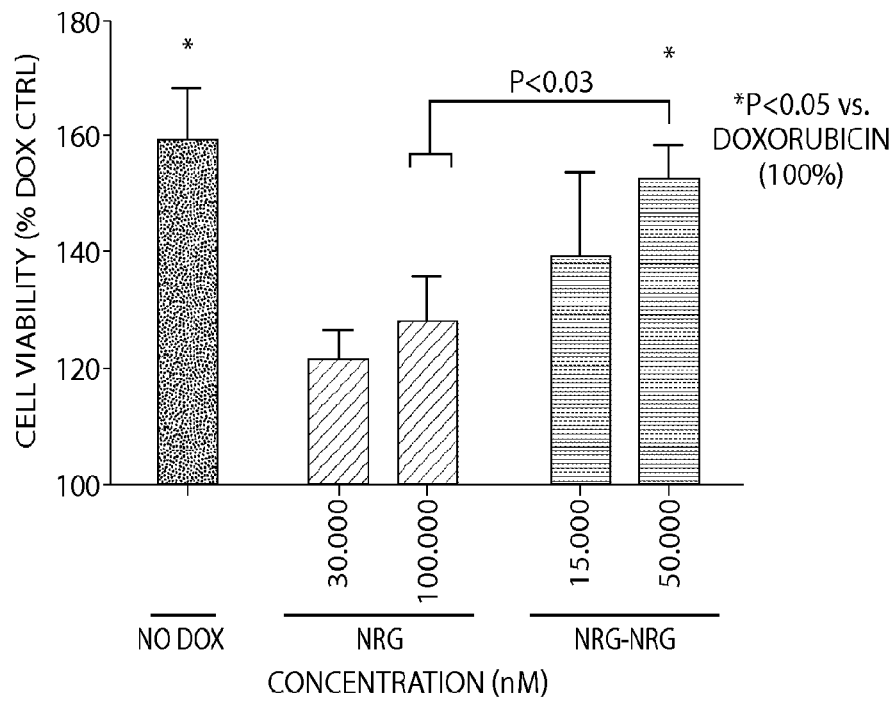
FIG. 6 is a bar graph showing the effect of NRG monomers and NRG homodimers on cardiomyocyte viability in the presence of doxorubicin.
Figure 7:
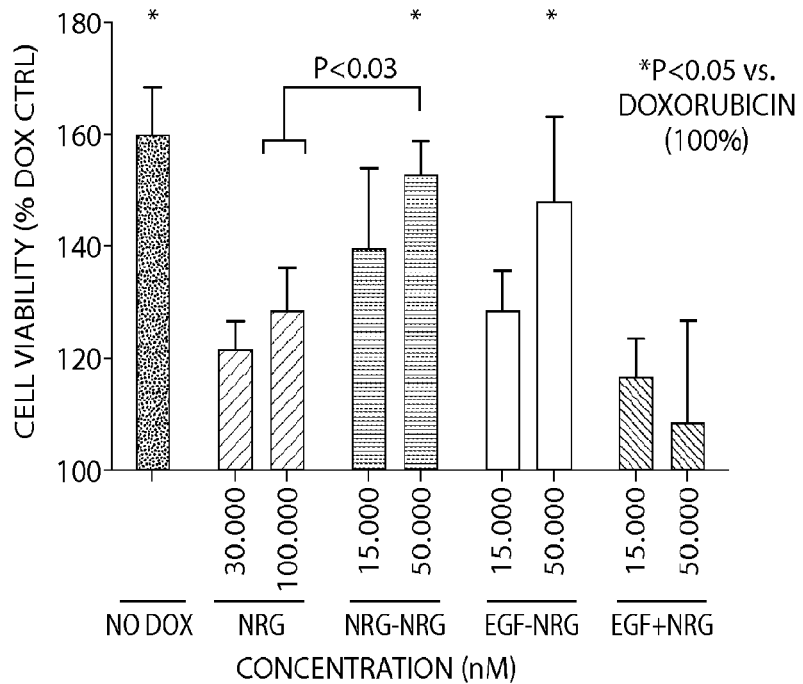
FIG. 7 is a bar graph showing the effect of NRG monomers, NRG homodimers, EGF-NRG heterodimers, and EGF and NRG monomers on cardiomyocyte viability in the presence of doxorubicin.
Figure 8A:
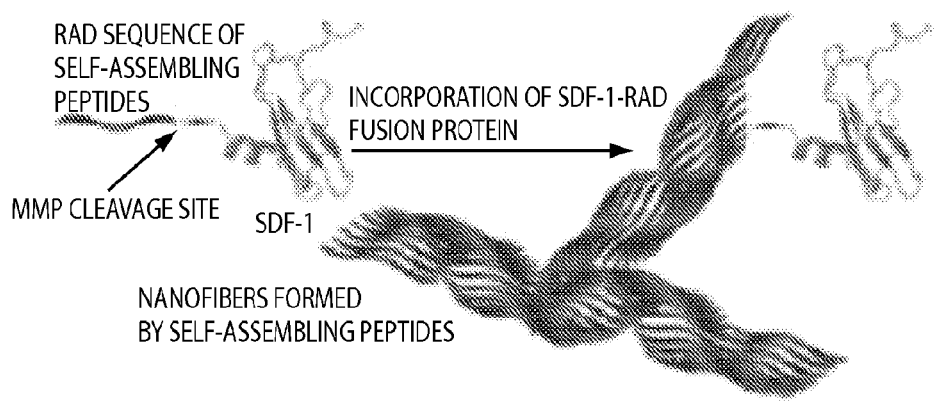
FIG. 8. Local delivery of proteins to the myocardium via self-assembling peptide nanofibers. (A) Schematic of SDF-1-RAD fusion proteins in self-assembling peptide nanofibers. (B) Mutation scheme for production of SDF-1(S4V), a protease resistant form of SDF-1. (C) Nanofiber delivery of SDF-1(S4V) results in increased capillary density in infarcted hearts as measured by isolectin-positive staining, n=7, values =mean ±SEM. From reference [10]; this experiment has been replicated in vivo 3 times.
Figure 8B:
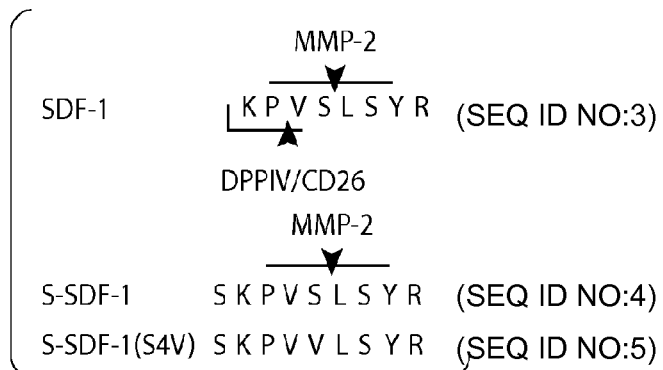
Figure 8C:
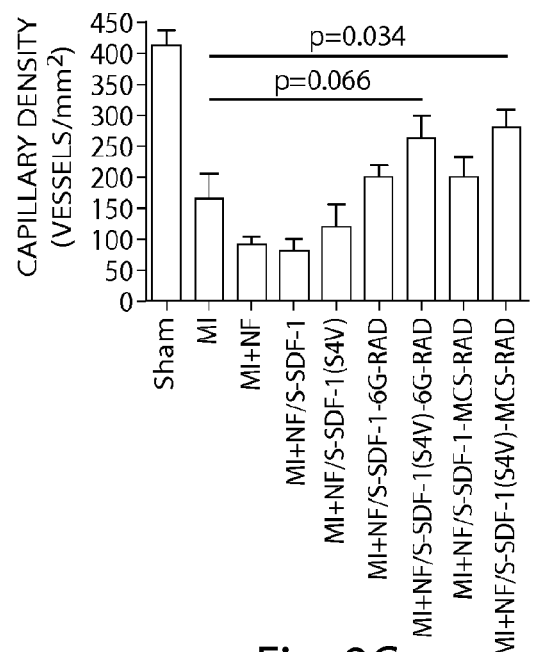

FIGS. 6 and 7 show similar results. FIG. 6 shows that the viability of cardiomyocytes is significantly ($p<0.05$) decreased in the presence of NRG monomers as compared to NRG homodimers, in the presence of doxorubicin. FIG. 7 shows that cardiomyocyte viability is increased in the presence of an EGF-NRG dimer relative to EGF and NRG used together as monomers.

Local Delivery of Proteins to the Heart Via Self-Assembling Peptide Nanofibers

Self-assembling peptide nanofibers can be used as a vehicle for local protein delivery to the myocardium. This biodegradable scaffold interacts well with cardiomyocytes in vitro [31] and has been used to successfully deliver numerous proteins in vivo [10-12, 32]. Several strategies for attachment of proteins to self-assembling peptides have been employed. One such strategy employed tethering of SDF-1 to self-assembling peptides by construction of fusion proteins consisting of the protein sequence and the sequence of self-assembling peptides (called RAD). The RAD sequence of this new fusion protein was shown to incorporate into the nanofiber scaffold during peptide self-assembly [10] (FIG. 6). Additionally, SDF-1-RAD incorporated in self-assembling peptides was detected in the myocardium up to 7 days after injection [10].

Figure 9A:
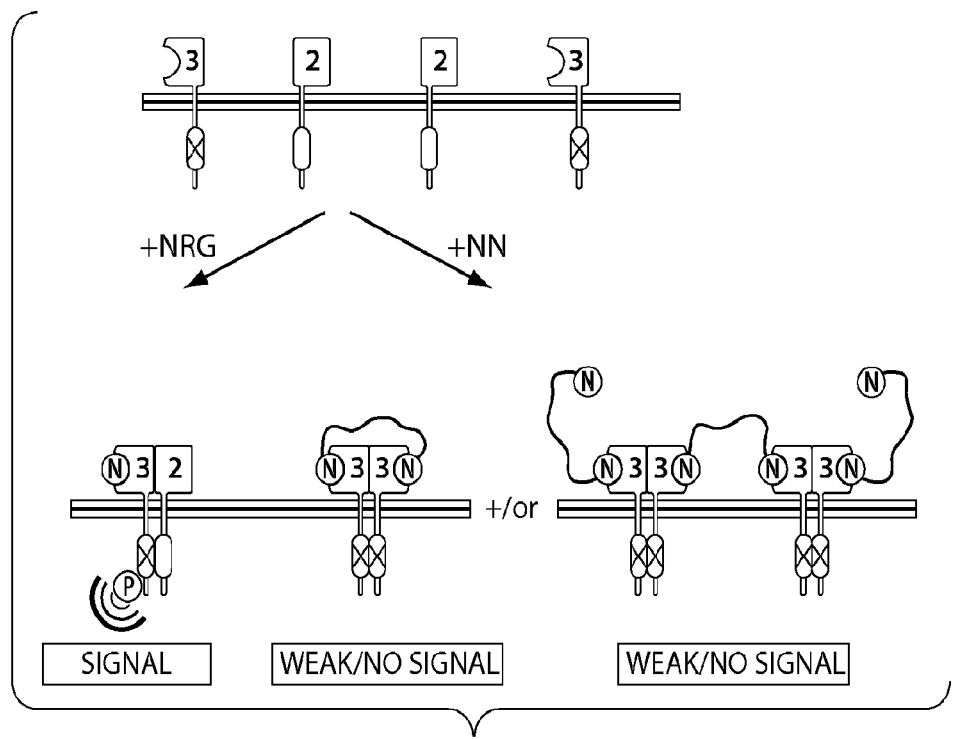
FIG. 9. Western blot analysis of pHER2 and pHER3 in lysates from H3255 cells stimulated by monovalent NRG (NC) or bivalent NRG (NN) (data representative of 2 independent experiments) (FIG. 9B). A possible mechanism for the observed differences in monovalent NRG compared to bivalent NN, in which NN fosters homodimerization or homo-oligomerization of HER3 at the expense of heterodimers with HER2, is illustrated in the schematic (FIG. 9A).
Figure 9B:
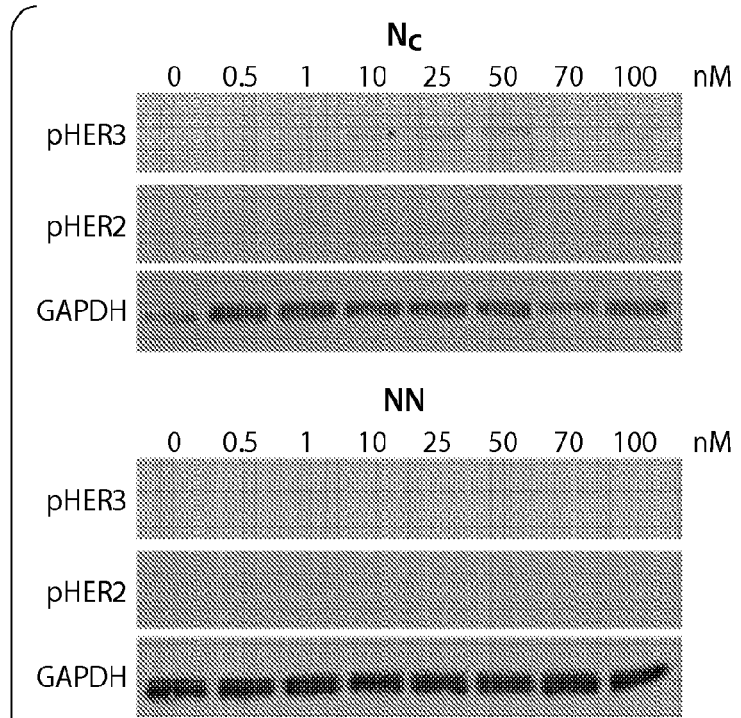

Bivalent Ligands May Induce Dimerization, Oligomerization, or Aggregation of ErbB Receptors It has been shown by western blot that monovalent Nrg stimulates phosphorylation of ErbB2 and ErbB3 receptors in H3255 cells (a non-small cell lung carcinoma cell line) in a dose-dependant manner, while bivalent Nrg (NN) does not (FIG. 9B). Based on the knowledge that its weak kinase domain prevents the ErbB3 receptor from generating a downstream signal when paired with another ErbB3 receptor, this absence of phosphorylation in the presence of NN suggests that NN induces dimerization, oligomerization, and/or aggregation of ErbB3 receptors (FIG. 9A). This hypothesis is further supported by the use of H3255 cells, which express high levels of the ErbB3 receptor and low levels of the ErbB4 receptor. Because the potential phenotypic effects associated with dimerization, oligomerization, and/or aggregation are more apparent with ErbB3 than ErbB4, this setting was chosen for proof-of-concept experiments.

Bivalent Ligands Induce Aggregation of Soluble ErbB Receptors

Figure 10:
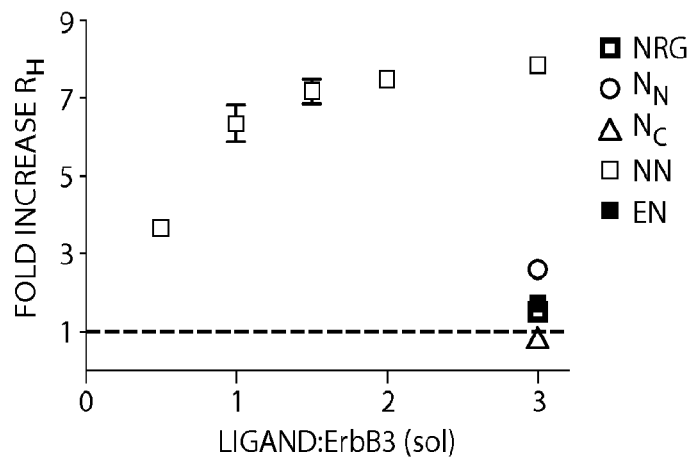
FIG. 10. Specific binding of bivalent NN to HER3. Bivalent NN, monovalent NRG ($N_C$ and $N_N$), native NRG, or bivalent EN were exposed to soluble crosslinked HER3 homodimers (ErbB3) and hydrodynamic radius ($R_H$) at various ligand:ErbB3 ratios. Receptor aggregation was determined by dynamic light scattering (n=10). Only bivalent NN induced aggregation of soluble ErbB3 receptors, indicating specific binding of both Nrg-1B domains of NN to distinct ErbB3 receptors.

Nrg-1B binds both ErbB3 and ErbB4 receptors with high affinity, however only ErbB4 spontaneously aggregates in solution when exposed to Nrg-1B, and ErbB3 only aggregates if both Nrg-1B domains of bivalent Nrg are functional and able to bind their own receptor. To assess whether the bivalent ligands are functional and thus able to induce aggregation of soluble ErbB4 receptor domains in solution, one ligand-receptor complex was physically tethered to another. Increasing aggregation of soluble ErbB4 receptor in solution up until a point where the receptor:ligand ratio was >1 (FIG. 10) was observed. These data provide further evidence that each protein domain of the bivalent ligand interacts with a cognate receptor based on affinity and thus drives dimerization/oligomerization/aggregation, leading to differential downstream signaling compared to the native protein.

Bivalent Ligands do not Reduce Cytotixic Activity of Doxorubicin

Figure 11:
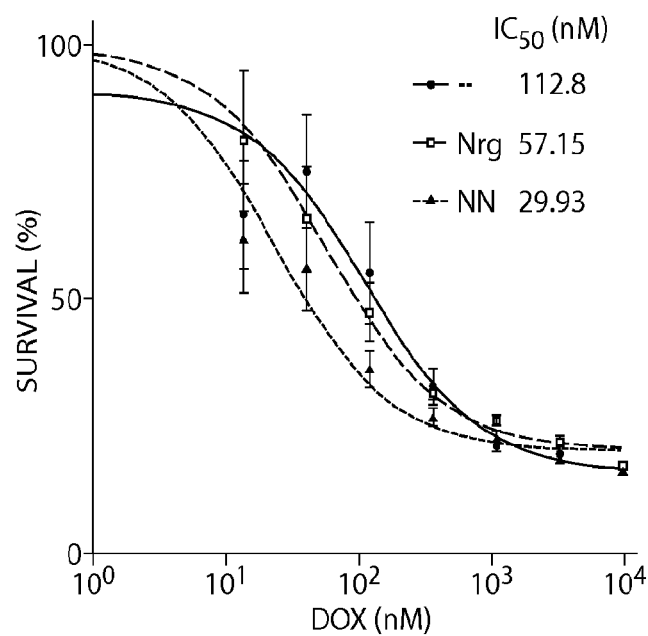
FIG. 11. Bivalent NRG does not diminish the cytotoxic activity of DOX on cancer cells. SK-BR-3 human breast cancer cells were simultaneously exposed to varying concentrations of DOX and either growth media (--), growth media+ 50 nM native NRG (Nrg) or growth media+25 nM bivalent NRG (NN). $IC_{50}$ values, calculated from the resulting non-linear best-fit lines using GraphPad Prism software, indicate that bivalent NRG does not reduce the potency of DOX against these cells.

SK-BR-3 human breast cancer cells were simultaneously exposed to varying concentrations of DOX and either growth media (--), growth media+50 nM native NRG (Nrg), or growth media+25 nM bivalent NRG (NN). $IC_{50}$ values, calculated from the resulting non-linear best-fit lines using GraphPad Prism software, indicated that NN does not reduce the potency of DOX against these cells. These data suggest that the cardioprotective activity NN results from induction of a separate pathway (e.g., induced ErbB4 dimerization, oligomerization, and/or aggregation) (FIG. 11).

REFERENCES

1. Maradia, K. and M. Guglin, *Pharmacologic prevention of anthracycline-induced cardiomyopathy*. Cardiology in review, 2009. 17(5): p. 243-52.
2. Rayson, D., et al., *Anthracycline-trastuzumab regimens for HER2/neu-overexpressing breast cancer: current experience and future strategies*. Ann Oncol, 2008. 19(9): p. 1530-9.
3. Wouters, K. A., et al., *Protecting against anthracycline-induced myocardial damage: a review of the most promising strategies*. Br J Haematol, 2005. 131(5): p. 561-78.
4. Bian, Y., et al., *Neuregulin-1 Attenuated Doxorubicin-Induced Decrease in Cardiac Troponins*. Am J Physiol Heart Circ Physiol, 2009.
5. Liu, X., et al., *Neuregulin-1/erbB-activation improves cardiac function and survival in models of ischemic, dilated, and viral cardiomyopathy*. J Am Coll Cardiol, 2006. 48(7): p. 1438-47.
6. Bersell, K., et al., *Neuregulinl/ErbB4 signaling induces cardiomyocyte proliferation and repair of heart injury*. Cell, 2009. 138(2): p. 257-70.
7. Fuller, S. J., K. Sivarajah, and P. H. Sugden, *ErbB receptors, their ligands, and the consequences of their activation and inhibition in the myocardium*. Journal of Molecular and Cellular Cardiology, 2008. 44(5):p. 831-54.
8. Jones, J. T., R. W. Akita, and M. X. Sliwkowski, *Binding specificities and affinities of egf domains for ErbB receptors*. FEBS Lett, 1999. 447(2-3): p. 227-31.
9. Fukazawa, R., et al., *Neuregulin-1 protects ventricular myocytes from anthracycline-induced apoptosis via erbB4-dependent activation of PI3-kinase/Akt*. Journal of Molecular and Cellular Cardiology, 2003. 35(12): p. 1473-9.
10. Segers, V. F., et al., *Local delivery of protease-resistant stromal cell derived factor-1 for stem cell recruitment after myocardial infarction*. Circulation, 2007. 116(15): p. 1683-92.
11. Hsieh, P. C. H., et al., *Controlled delivery of PDGF-BB for myocardial protection using injectable selfassembling peptide nanofibers*. Journal of Clinical Investigation, 2006. 116(1): p. 237-48.
12. Hsieh, P. C. H., et al., *Local controlled intramyocardial delivery of platelet-derived growth factor improves postinfarction ventricular function without pulmonary toxicity*. Circulation, 2006. 114(7): p. 637-44.
13. Rahman, A., N. More, and P. S. Schein, *Doxorubicin-induced chronic cardiotoxicity and its protection by liposomal administration*. Cancer Research, 1982. 42(5): p. 1817-25.
14. Park, J., et al., *PEGylated PLGA nanoparticles for the improved delivery of doxorubicin*. Nanomedicine: nanotechnology, biology, and medicine, 2009.
15. Crone, S. A., et al., *ErbB2 is essential in the prevention of dilated cardiomyopathy*. Nat Med, 2002. 8(5): p. 459-65.
16. Yarden, Y. and M. X. Sliwkowski, *Untangling the ErbB signalling network*. Nat Rev Mol Cell Biol, 2001. 2(2): p. 127-37.
17. Kuramochi, Y., X. Guo, and D. B. Sawyer, *Neuregulin activates erbB2-dependent src/FAK signaling and cytoskeletal remodeling in isolated adult rat cardiac myocytes*. Journal of Molecular and Cellular Cardiology, 2006. 41(2): p. 228-35.
18. Tzahar, E., et al., *Bivalence of EGF-like ligands drives the ErbB signaling network*. EMBO J, 1997. 16(16): p. 4938-50.
19. Kühn, B., et al., *Periostin induces proliferation of differentiated cardiomyocytes and promotes cardiac repair*. Nat Med, 2007. 13(8): p. 962-9.
20. Moll, J. R., et al., *Designed heterodimerizing leucine zippers with a ranger of pIs and stabilities up to 0(−15) M*. Protein Sci, 2001. 10(3): p. 649-55.
21. Ogiso, H., et al., *Crystal structure of the complex of human epidermal growth factor and receptor extracellular domains*. Cell, 2002. 110(6): p. 775-87.
22. Martin, A., T. A. Baker, and R. T. Sauer, *Rebuilt AAA+ motors reveal operating principles for ATPfuelled machines*. Nature, 2005. 437(7062): p. 1115-20.

23. Leader, B., Q. J. Baca, and D. E. Golan, *Protein therapeutics: a summary and pharmacological classification.* Nat Rev Drug Discov, 2008. 7(1): p. 21-39.
24. Tayalia, P. and D. J. Mooney, *Controlled Growth Factor Delivery for Tissue Engineering.* Adv. Mater., 2009: p. NA-NA.
25. Zhang, S., *Fabrication of novel biomaterials through molecular self-assembly.* Nat. Biotechnol., 2003. 21(10): p. 1171-1178.
26. Zhang, S., *Emerging biological materials through molecular self-assembly.* Biotechnol Adv, 2002. 20(5-6): p. 321-39.
27. Caplan, M. R., et al., *Self-assembly of a beta-sheet protein governed by relief of electrostatic repulsion relative to van der Waals attraction.* Biomacromolecules, 2000. 1(4): p. 627-31.
28. Caplan, M. R., et al., *Control of self-assembling oligopeptide matrix formation through systematic variation of amino acid sequence.* Biomaterials, 2002. 23(1): p. 219-27.
29. Wiley, H. S., *Trafficking of the ErbB receptors and its influence on signaling.* Exp Cell Res, 2003. 284(1): p. 78-88.
30. Sawyer, D. B., et al., *Modulation of anthracycline-induced myofibrillar disarray in rat ventricular myocytes by neuregulin-1beta and anti-erbB2: potential mechanism for trastuzumab-induced cardiotoxicity.* Circulation, 2002. 105(13): p. 1551-4.
31. Narmoneva, D. A., et al., *Self-assembling short oligopeptides and the promotion of angiogenesis.* Biomaterials, 2005. 26(23): p. 4837-46.
32. Davis, M. E., et al., *Local myocardial insulin-like growth factor 1 (IGF-1) delivery with biotinylated peptide nanofibers improves cell therapy for myocardial infarction.* Proc Natl Acad Sci USA, 2006. 103(21): p. 8155-60.
33. Barbacci, E. G., et al., *The structural basis for the specificity of epidermal growth factor and heregulin binding.* J Biol Chem, 1995. 270(16): p. 9585-9.
34. Sohy, D., et al., *Hetero-oligomerization of CCR2, CCR5 and CXCR4 and the protean effects of "selective"-antagonists.* J Biol Chem, 2009.
35. Zhao, Y. Y., et al., *Neuregulins promote survival and growth of cardiac myocytes. Persistence of ErbB2 and ErbB4 expression in neonatal and adult ventricular myocytes.* J Biol Chem, 1998. 273(17): p. 10261-9.
36. Pentassuglia, L., et al., *Inhibition of ErbB2 by receptor tyrosine kinase inhibitors causes myofibrillar structural damage without cell death in adult rat cardiomyocytes.* Exp Cell Res, 2009. 315(7): p. 1302-12.
37. Ueno, M., et al., *Doxorubicin induces apoptosis by activation of caspase-3 in cultured cardiomyocytes in vitro and rat cardiac ventricles in vivo.* J Pharmacol Sci, 2006. 101(2): p. 151-8.
38. Alvarado, D., D. E. Klein, and M. A. Lemmon, *ErbB2 resembles an autoinhibited invertebrate epidermal growth factor receptor.* Nature, 2009. 461(7261): p. 287-91.
39. Li, P., et al., *Design and synthesis of paclitaxel conjugated with an ErbB2-recognizing peptide, EC-1.* Biopolymers, 2007. 87(4): p. 225-30.
40. Padin-Iruegas, M. E., et al., *Cardiac progenitor cells and biotinylated insulin-like growth factor-1 nanofibers improve endogenous and exogenous myocardial regeneration after infarction.* Circulation, 2009. 120(10): p. 876-87.
41. Hsieh, P. C., et al., *Evidence from a genetic fate-mapping study that stem cells refresh adult mammalian cardiomyocytes after injury.* Nat Med, 2007. 13(8): p. 970-4.
42. Lechene, C., et al., *High-resolution quantitative imaging of mammalian and bacterial cells using stable isotope mass spectrometry.* J Biol, 2006. 5(6): p. 20.
43. Lechene, C. P., et al., *Quantitative imaging of nitrogen fixation by individual bacteria within animal cells.* Science, 2007. 317(5844): p. 1563-6.
44. Davis, M. E., et al., *Custom design of the cardiac microenvironment with biomaterials.* Circulation Research, 2005. 97(1): p. 8-15.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for reducing anthracycline-associated cardiotoxicity comprising
administering to a subject in need of anthracycline therapy and reduced anthracycline-associated cardiotoxicity a neuregulin dimer, or a ligand dimer, in an amount effective to reduce anthracycline-associated cardiotoxicity, wherein each of the ligands of the ligand dimer comprises an epidermal growth factor (EGF), a neuregulin, or a spitz.

2. The method of claim 1, wherein the anthracycline therapy is doxorubicin.

3. The method of claim 1, wherein the subject is administered the neuregulin dimer, or the ligand dimer, prior to the anthracycline therapy.

4. The method of claim 1, wherein the subject is administered the neuregulin dimer, or the ligand dimer, after the anthracycline therapy.

5. The method of claim 1, wherein the neuregulin dimer, or the ligand dimer, is administered locally to the heart.

6. The method of claim 1, wherein the subject is administered an amount of anthracycline therapy above the normally administered amount.

7. The method of claim 1, wherein the neuregulin dimer, or the ligand dimer, is administered in a sustained release formulation.

8. (Withdrawn and Previously Presented) The method of claim 1, wherein the ligand dimer is an EGF dimer or a spitz dimer.

9. The method of claim 1, wherein the ligand dimer comprises a neuregulin and an EGF, a spitz and a neuregulin, or a spitz and an EGF.

10. A method for increasing anthracycline tolerable dose comprising
administering to a subject in need of anthracycline therapy a neuregulin dimer and an anthracycline, or a ligand dimer and an anthracycline, wherein each of the ligands of the ligand dimer comprises an epidermal growth factor (EGF), a neuregulin, or a spitz, and wherein the anthracycline is administered in an amount above the normally administered amount.

11. A method for treating a subject comprising
administering to a subject who is experiencing or has experienced a myocardial infarction a neuregulin dimer, or a ligand dimer, in an amount effective to reduce infarct size, wherein each of the ligands of the ligand dimer comprises an epidermal growth factor (EGF), a neuregulin, or a spitz.

12. A method for treating a subject comprising
administering to a subject having heart failure a neuregulin dimer, or a ligand dimer, in an amount effective to treat the subject, wherein each of the ligands of the ligand dimer comprises an epidermal growth factor (EGF), a neuregulin, or a spitz.

* * * * *